US012784915B2

(12) United States Patent
Reichlin et al.

(10) Patent No.: US 12,784,915 B2
(45) Date of Patent: Nov. 3, 2026

(54) SYSTEMS AND METHODS FOR PSYCHIATRIC SCREENING AND ASSESSMENT

(71) Applicant: PsychNow, Inc., Chicago, IL (US)

(72) Inventors: Aaron Scott Reichlin, Evanston, IL (US); Alexander Mueller, Barrington, RI (US); Eleni Adamidi, Athens (GR); Entmont-Grigoris Ntervakos, Athens (GR)

(73) Assignee: PsychNow, Chicago, IL (US)

( * ) Notice: Subject to any disclaimer, the term of this patent is extended or adjusted under 35 U.S.C. 154(b) by 0 days.

(21) Appl. No.: 19/098,446

(22) Filed: Apr. 2, 2025

(65) Prior Publication Data

US 2025/0308704 A1 Oct. 2, 2025

Related U.S. Application Data

(60) Provisional application No. 63/713,650, filed on Oct. 30, 2024, provisional application No. 63/573,546, filed on Apr. 3, 2024.

(30) Foreign Application Priority Data

Apr. 2, 2024 (GR) .............................. 20240100233

(51) Int. Cl.
*G16H 50/30* (2018.01)
*G06F 40/40* (2020.01)
(Continued)

(52) U.S. Cl.
CPC ............. *G16H 50/30* (2018.01); *G06F 40/40* (2020.01); *G16H 10/60* (2018.01); *G16H 80/00* (2018.01)

(58) Field of Classification Search
None
See application file for complete search history.

(56) References Cited

U.S. PATENT DOCUMENTS 7,617,116 B2 11/2009 Amar et al.
7,720,701 B2 5/2010 Richards et al.
(Continued)

FOREIGN PATENT DOCUMENTS

WO 2001/087158 A1 11/2001
WO WO-2020102223 A2 * 5/2020 ......... A61B 5/14551
(Continued)

OTHER PUBLICATIONS

Huan-Chung Li et al., Make patient consultation warmer: A clinical application for speech emotion recognition, 11 Applied Sciences 4782 (2021), https://www.mdpi.com/2076=3417/11/11/4782 (Year: 2021).*

(Continued)

*Primary Examiner* — Jonathon A. Szumny
*Assistant Examiner* — Nicholas Akogyeram, II
(74) *Attorney, Agent, or Firm* — Bookoff McAndrews, PLLC

(57) ABSTRACT

Various embodiments of this disclosure relate generally to utilizing a health control system. The method comprises receiving user data from one or more first data stores, analyzing the user data to determine a plurality of queries, outputting the plurality of queries, in response to the outputting, receiving user response data, creating user overview data by applying one or more language learning models to the user response data and the user data, determining whether the user overview data includes one or more incongruencies by applying one or more trained first machine-learning models to the user overview data, in response to determining inclusion of the one or more incongruencies, (Continued)

extracting the user overview data that corresponds to the one or more incongruencies, generating an alert by applying the one or more trained first machine-learning models to the user overview data and the one or more incongruencies, if included, and outputting the alert.

23 Claims, 11 Drawing Sheets

(51) Int. Cl.
*G16H 10/60* (2018.01)
*G16H 80/00* (2018.01)

(56) References Cited

U.S. PATENT DOCUMENTS

| | | | |
|---|---|---|---|
| 7,733,776 | B1 | 6/2010 | Lee et al. |
| 7,835,928 | B2 | 11/2010 | Schoenberg |
| 7,890,345 | B2 | 2/2011 | Schoenberg |
| 7,895,061 | B2 | 2/2011 | Schoenberg |
| 7,937,275 | B2 | 5/2011 | Schoenberg |
| 8,249,898 | B2 | 8/2012 | Schoenberg |
| 8,332,287 | B2 | 12/2012 | Gee et al. |
| 8,463,620 | B2 | 6/2013 | Schoenberg |
| 8,504,382 | B2 | 8/2013 | Schoenberg |
| 8,510,128 | B2 | 8/2013 | Schoenberg |
| 8,510,130 | B2 | 8/2013 | Schoenberg |
| 8,515,776 | B2 | 8/2013 | Schoenberg |
| 8,521,553 | B2 | 8/2013 | Schoenberg |
| 8,561,882 | B2 | 10/2013 | Stone et al. |
| 8,600,773 | B2 | 12/2013 | Schoenberg |
| 8,639,532 | B2 | 1/2014 | Schoenberg |
| 8,660,858 | B2 | 2/2014 | Mullin et al. |
| 8,671,112 | B2 | 3/2014 | Amar et al. |
| 8,719,047 | B2 | 5/2014 | Schoenberg |
| 8,756,071 | B2 | 6/2014 | Nix et al. |
| 8,856,000 | B1 | 10/2014 | Larsen et al. |
| 9,015,609 | B2 | 4/2015 | Schoenberg |
| 9,305,286 | B2 | 4/2016 | Larsen et al. |
| 9,372,916 | B2 | 6/2016 | Stone et al. |
| 9,578,152 | B2 | 2/2017 | Schoenberg |
| 9,672,325 | B2 | 6/2017 | Robinson et al. |
| 9,678,636 | B2 | 6/2017 | Schoenberg |
| 9,685,174 | B2 | 6/2017 | Karam et al. |
| 9,805,163 | B1 | 10/2017 | Panch et al. |
| 9,817,949 | B2 | 11/2017 | Poulin et al. |
| 9,830,475 | B2 | 11/2017 | Khandelwal |
| 9,971,873 | B2 | 5/2018 | Schoenberg |
| 10,083,365 | B2 | 9/2018 | Schiller et al. |
| 10,242,345 | B2 | 3/2019 | Taylor et al. |
| 10,268,966 | B2 | 4/2019 | Mould |
| 10,347,382 | B2 | 7/2019 | Nix et al. |
| D859,418 | S | 9/2019 | Baird et al. |
| 10,438,135 | B2 | 10/2019 | Larsen et al. |
| 10,517,521 | B2 | 12/2019 | el Kaliouby et al. |
| 10,528,916 | B1 | 1/2020 | Taylor et al. |
| 10,685,329 | B2 | 6/2020 | Taylor et al. |
| 10,748,644 | B2 | 8/2020 | Shriberg et al. |
| 11,013,861 | B2 | 5/2021 | Wehba et al. |
| 11,120,895 | B2 | 9/2021 | Shriberg et al. |
| 11,176,444 | B2 | 11/2021 | Wall et al. |
| 11,232,408 | B2 | 1/2022 | Taylor et al. |
| 11,233,839 | B2 | 1/2022 | Hurst et al. |
| 11,250,935 | B2 | 2/2022 | Shanbhag |
| 11,257,041 | B2 | 2/2022 | Larsen et al. |
| 11,430,567 | B2 | 8/2022 | Johnstone et al. |
| 11,468,242 | B1 | 10/2022 | Coppersmith et al. |
| 11,501,863 | B2 | 11/2022 | Mould |
| 11,589,003 | B2 | 2/2023 | Schoenberg |
| 11,611,690 | B2 | 3/2023 | Abbas |
| 11,682,033 | B1 | 6/2023 | Hahr et al. |
| 2004/0047286 | A1 | 3/2004 | Larsen et al. |
| 2005/0228236 | A1 | 10/2005 | Diederich et al. |
| 2006/0074710 | A1 | 4/2006 | Funk et al. |
| 2007/0245360 | A1 | 10/2007 | Alexander, Jr. et al. |
| 2008/0065415 | A1 | 3/2008 | Swain et al. |
| 2008/0103836 | A1 | 5/2008 | Park et al. |
| 2008/0126133 | A1 | 5/2008 | Park |
| 2009/0192821 | A9 | 7/2009 | Park et al. |
| 2010/0293004 | A1 | 11/2010 | Nye et al. |
| 2011/0313784 | A1 | 12/2011 | Harvey et al. |
| 2012/0059663 | A1 | 3/2012 | Levesque et al. |
| 2012/0173258 | A1 | 7/2012 | Hofmann et al. |
| 2012/0253868 | A1 | 10/2012 | Ach et al. |
| 2013/0046551 | A1 | 2/2013 | Vahle et al. |
| 2013/0332186 | A1 | 12/2013 | Epstein et al. |
| 2014/0108043 | A1 | 4/2014 | Ach et al. |
| 2014/0207475 | A1 | 7/2014 | Ach et al. |
| 2014/0214450 | A1 | 7/2014 | Bechtold et al. |
| 2014/0215301 | A1 | 7/2014 | Stone et al. |
| 2015/0127358 | A1 | 5/2015 | Porter et al. |
| 2015/0154564 | A1 | 6/2015 | Moon et al. |
| 2015/0242819 | A1 | 8/2015 | Moses et al. |
| 2016/0127343 | A1 | 5/2016 | Schiller et al. |
| 2019/0216334 | A1 | 7/2019 | Zhou |
| 2019/0362326 | A1 | 11/2019 | Nguyen et al. |
| 2019/0385711 | A1 | 12/2019 | Shriberg et al. |
| 2020/0106851 | A1 | 4/2020 | de Waal |
| 2020/0167786 | A1* | 5/2020 | Kursun ................... H04L 63/08 |
| 2020/0321082 | A1 | 10/2020 | Shriberg et al. |
| 2020/0387850 | A1 | 12/2020 | Kramer et al. |
| 2020/0388287 | A1* | 12/2020 | Anushiravani ...... G06N 3/0475 |
| 2021/0110895 | A1* | 4/2021 | Shriberg ................ G16H 10/20 |
| 2022/0130518 | A1* | 4/2022 | Ozen Irmak ........... G16H 50/30 |
| 2022/0165393 | A1* | 5/2022 | Inz ....................... A61B 5/7264 |
| 2022/0199205 | A1 | 6/2022 | Shriberg et al. |
| 2022/0270716 | A1 | 8/2022 | Shriberg et al. |
| 2022/0374115 | A1 | 11/2022 | Rankin et al. |
| 2022/0374848 | A1 | 11/2022 | Rankin et al. |
| 2023/0004954 | A1 | 1/2023 | Ammatanda et al. |
| 2023/0071217 | A1 | 3/2023 | Sontag et al. |
| 2023/0153772 | A1 | 5/2023 | Nguyen et al. |
| 2023/0267229 | A1 | 8/2023 | Shea et al. |
| 2023/0274242 | A1 | 8/2023 | Ammatanda et al. |
| 2023/0274348 | A1 | 8/2023 | Ammatanda et al. |
| 2023/0316322 | A1 | 10/2023 | Ammatanda et al. |
| 2023/0351572 | A1* | 11/2023 | Qiu ........................ G06N 3/042 |
| 2023/0360049 | A1 | 11/2023 | Ammatanda et al. |
| 2024/0087752 | A1 | 3/2024 | Rutowski et al. |
| 2024/0170109 | A1 | 5/2024 | Shriberg et al. |
| 2024/0179200 | A1 | 5/2024 | Hurst et al. |
| 2024/0350096 | A1* | 10/2024 | Halpern ................. A61B 5/747 |

FOREIGN PATENT DOCUMENTS

| | | | |
|---|---|---|---|
| WO | 2020/206178 | A1 | 10/2020 |
| WO | 2021/081418 | A1 | 4/2021 |
| WO | 2022/72147 | A1 | 4/2022 |

OTHER PUBLICATIONS

Clinical Neuroanatomy Seminars, "#CNStalks: Using machine learning to predict mental health—Andre Marquand," Mar. 31, 2022, Retrieved from the Internet on Apr. 2, 2025, URL: https://www.youtube.com/watch?v=8YX1K_In14k.
TEDx Talks, "Artificial Intelligence Meets Mental Health Therapy | Andy Blackwell | TEDxNatick," Mar. 11, 2020, Retrieved from the Internet on Apr. 2, 2025, URL: https://www.youtube.com/watch?v=ZkTvw3usMw4.
BrainMind Summit, "Rosalind Picard—How Well Can We Forecast, and Change, your Future Mental Health?," May 24, 2019, Retrieved from the Internet on Apr. 2, 2025, URL: https://www.youtube.com/watch?v=hur0KnA_okl.
King's College London, "Artificial Intelligence for Mental Health and Neuroscience," Sep. 18, 2019, Retrieved from the Internet on Apr. 2, 2025, URL: https://www.youtube.com/watch?v=_TU3yhnbzz0.
Victor Panlilio Photography, "Machine Learning in Psychiatry," Mar. 31, 2018, Retrieved from the Internet on Apr. 2, 2025, URL: https://www.youtube.com/watch?v=d_iwPQG_iXk.

(56) References Cited

OTHER PUBLICATIONS

University of Alberta, "Machine learning and mental health: Research aims to make a more precise diagnosis of depression," Apr. 22, 2021, Retrieved from the Internet on Apr. 5, 2025, URL: https://www.youtube.com/watch?v=KlgP9NyCIKs.
Bill, "Mental Health Triage (Video)," Apr. 15, 2013, Retrieved from the Internet on Apr. 2, 2025, URL: https://www.youtube.com/watch?v=vDeBrgDFTGk.
The Transmitter, Sarah Deweerdt, "Triage may help speed up autism diagnosis, researchers say," Mar. 18, 2013, Retrieved from the Internet on Apr. 2, 2025, URL: https://www.thetransmitter.org/spectrum/triage-may-help-speed-up-autism-diagnosis-researchers-say/?fspec=1.
Aronson, "Medication errors: what they are, how they happen, and how to avoid them," May 20, 2009, vol. 102, Issue 7, Abstract only.
Boussadi et al., "Validity of a clinical decision rule-based alert system for drug dose adjustment in patients with renal failure intended to improve pharmacists' analysis of medication orders in hospitals," International Journal of Medical Informatics, Oct. 2013, vol. 82, Issue 10: pp. 964-972, Abstract only.
Seto et al., "Developing healthcare rule-based expert systems: Case study of a heart failure telemonitoring system." International Journal of Medical Informatics, Aug. 2012, vol. 81, Issue 8: pp. 556-565, Abstract only.

* cited by examiner

320

340

350

500

SYSTEMS AND METHODS FOR PSYCHIATRIC SCREENING AND ASSESSMENT

CROSS REFERENCE TO RELATED APPLICATIONS

This application claims priority to U.S. Provisional Application No. 63/713,650, filed on Oct. 30, 2024, U.S. Provisional Application No. 63/573,546, filed on Apr. 3, 2024, and Greek application No. 20240100233, filed on Apr. 2, 2024, which are incorporated by reference herein in their entireties.

TECHNICAL FIELD

Various embodiments of this disclosure relate generally to systems and methods for training and utilizing artificial intelligence for a health control system.

BACKGROUND

Traditional psychiatric assessment methods typically rely heavily on patient self-reports during patient assessment. However, the mental health industry has known about the unreliability of patient self-reporting for decades. For example, patients may under-report data or over-report data. Additionally, there are no easily administered objective tests for diagnosing most mental disorders and/or identifying the biopsychosocial factors that cause a patient's distress. Nonetheless, patient self-reports are used extensively because no practical alternative exists. As a result, a need exists for increasing the accuracy in patient-reported data in mental health care systems.

This disclosure is directed to addressing one or more of the above-referenced challenges. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY OF THE DISCLOSURE

According to certain aspects of the disclosure, embodiments are disclosed for utilizing a health control system.

In one aspect, an exemplary embodiment of a method for utilizing a health control system is disclosed. The method may include receiving, by one or more processors, user data from one or more first data stores, wherein the user data includes user health information. The method may further include analyzing, by the one or more processors, the user data to determine a plurality of queries, wherein the plurality of queries include one or more audio queries, one or more text queries, and/or one or more video queries, and wherein the plurality of queries are received from a knowledge base. The method may further include outputting, by the one or more processors, the plurality of queries via a user device, wherein the outputting includes displaying at least one of the plurality of queries on an interface of the user device and/or outputting at least one of the plurality of queries using an audio interface or a video interface of the user device. The method may further include, in response to the outputting, receiving, by the one or more processors, user response data from the one or more first data stores, a second data store, the interface, the audio interface, and/or the video interface of the user device. The method may further include creating, by the one or more processors, user overview data by applying one or more language learning models to the user response data and the user data. The method may further include determining, by the one or more processors, whether the user overview data includes one or more incongruencies by applying one or more trained first machine-learning models to the user overview data. The method may further include, in response to determining inclusion of the one or more incongruencies, extracting, by the one or more processors, via one or more trained second machine-learning models, the user overview data that corresponds to the one or more incongruencies. The method may further include generating, by the one or more processors, an alert by applying the one or more trained first machine-learning models to the user overview data and the one or more incongruencies, if included. The method may further include outputting, by the one or more processors, the alert to a display of a provider device.

In one aspect, a computer system for utilizing a health control system is disclosed. The computer system may comprise a memory having processor-readable instructions stored therein and one or more processors configured to access the memory and execute the processor-readable instructions, which when executed by the one or more processors configures the one or more processors to perform a plurality of functions. The functions may include receiving user data from one or more first data stores, wherein the user data includes user health information. The functions may further include analyzing the user data to determine a plurality of queries, wherein the plurality of queries include one or more audio queries, one or more text queries, and/or one or more video queries, and wherein the plurality of queries are received from a knowledge base. The functions may further include outputting the plurality of queries via a user device, wherein the outputting includes displaying at least one of the plurality of queries on an interface of the user device and/or outputting at least one of the plurality of queries using an audio interface or a video interface of the user device. The functions may further include, in response to the outputting, receiving user response data from the one or more first data stores, a second data store, the interface, the audio interface, and/or the video interface of the user device. The functions may further include creating user overview data by applying one or more language learning models to the user response data and the user data. The functions may further include determining whether the user overview data includes one or more incongruencies by applying one or more trained machine-learning models to the user overview data. The functions may further include, in response to determining inclusion of the one or more incongruencies, extracting, via one or more trained second machine-learning models, the user overview data that corresponds to the one or more incongruencies. The functions may further include generating an alert by applying the one or more trained first machine-learning models to the user overview data and the one or more incongruencies, if included. The functions may further include outputting the alert to a display of a provider device.

In one aspect, a non-transitory computer-readable medium containing instructions for utilizing a health control system is disclosed. The instructions may comprise receiving, by one or more processors, user data from one or more first data stores, wherein the user data includes user health information. The instructions may further comprise analyzing, by the one or more processors, the user data to determine a plurality of queries, wherein the plurality of queries include one or more audio queries, one or more text queries, and/or one or more video queries, and wherein the plurality of queries are received from a knowledge base. The instructions may further comprise outputting, by the one or more processors, the plurality of queries via a user device, wherein the outputting includes displaying at least one of the plurality of queries on an interface of the user device and/or outputting at least one of the plurality of queries using an audio interface or a video interface of the user device. The instructions may further comprise, in response to the outputting, receiving, by the one or more processors, user response data from the one or more first data stores, a second data store, the interface, the audio interface, and/or the video interface of the user device. The instructions may further comprise creating, by the one or more processors, user overview data by applying one or more language learning models to the user response data and the user data. The instructions may further comprise determining, by the one or more processors, whether the user overview data includes one or more incongruencies by applying one or more trained first machine-learning models to the user overview data. The instructions may further comprise, in response to determining inclusion of the one or more incongruencies, extracting, by the one or more processors, via one or more trained second machine-learning models, the user overview data that corresponds to the one or more incongruencies. The instructions may further comprise generating, by the one or more processors, an alert by applying the one or more trained first machine-learning models to the user overview data and the one or more incongruencies, if included. The instructions may further comprise outputting, by the one or more processors, the alert to a display of a provider device.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION OF EMBODIMENTS

Figure 1:
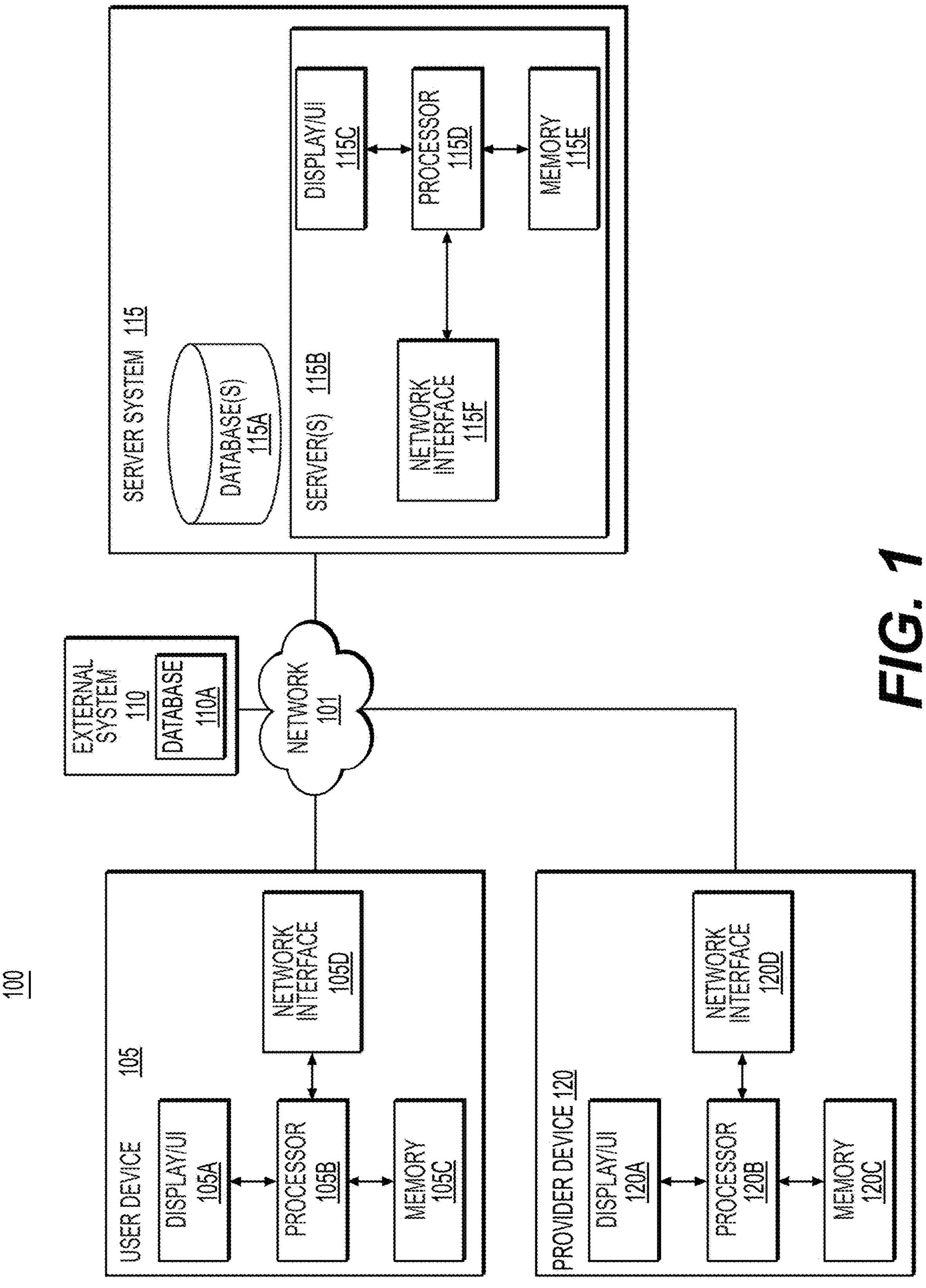
FIG. 1 depicts an exemplary networked computing environment that may be utilized with techniques presented herein, according to one or more embodiments.

According to certain aspects of the disclosure, methods and systems for training and utilizing artificial intelligence (AI) for a health control system are disclosed.

The systems and methods disclosed herein include many advantages. For example, the systems and methods allow for asynchronous monitoring and/or screening of a patient or a larger patient cohort without the necessity for conventional, in-person appointments by integrating a validation mechanism for patient self-reporting. Additional advantages may include leveraging the power of artificial intelligence (AI) and supervised learning to create an efficient and reliable heath control system. Additionally, the systems and methods leverage machine-assisted algorithms to validate the patient self-reports. Additional advantages may include determining a patient prioritization by using the machine-learning models to analyze extensive patient data in order to provide a recommendation regarding how patient caseloads should be prioritized. Additional advantages may include increased scalability, where the systems and methods may allow for the ability to screen/follow-up with a large number of patients. Additional advantages may include the increased ability to monitor patients in real-time, increased convenience for a patient and provider to have asynchronous communication, increased patient compliance due to convenience, and/or an increased ability to aggregate patient data across multiple systems to improve the tracking of patient data. Additional advantages may include utilizing machine-learning models to efficiently analyze an extraordinary amount of patient response data, create patient-specific summaries, generate quantitative ways to analyze qualitative data, as well as classify the response data. Thus, the systems and methods may improve the scalability and effectiveness of psychiatric services, ensure reliable patient self-reporting, and/or enable more efficient management of patient caseloads.

As will be discussed in more detail below, in various embodiments, systems and methods are described for training and utilizing artificial intelligence for a health control system. The systems and methods may include receiving, by one or more processors, user data from one or more data stores, wherein the user data includes user health information. The systems and methods may include analyzing, by the one or more processors, the user data to determine a plurality of queries. In other aspects, the systems and methods may not receive user data from one or more data stores, and, instead, the plurality of queries may be predetermined. The plurality of queries may include one or more audio queries, one or more text queries, and/or one or more video queries, and the plurality of queries may be received from a knowledge base. The systems and methods may include outputting, by the one or more processors, the plurality of queries via a user device, wherein the outputting includes displaying at least one of the plurality of queries on an interface of the user device and/or outputting at least one of the plurality of queries using an audio interface or a video interface of the user device. The systems and methods may include, in response to the outputting, receiving, by the one or more processors, user response data from the one or more first data stores, a second data store, the interface, the audio interface, and/or the video interface of the user device. The systems and methods may include creating, by the one or more processors, user overview data by applying one or more language learning models to the user response data and the user data. The systems and methods may include determining, by the one or more processors, whether the user overview data includes one or more incongruencies by applying one or more trained first machine-learning models to the user overview data. The systems and methods may include in response to determining inclusion of the one or more incongruencies, extracting, by the one or more processors, via one or more trained second machine-learning models, the user overview data that corresponds to the one or more incongruencies. The systems and methods may include generating, by the one or more processors, an alert by applying the one or more trained first machine-learning models to the user overview data and the one or more incongruencies, if included. The systems and methods may include outputting, by the one or more processors, the alert to a provider device.

The terminology used below may be interpreted in its broadest reasonable manner, even though it is being used in conjunction with a detailed description of certain specific examples of the present disclosure. Indeed, certain terms may even be emphasized below; however, any terminology intended to be interpreted in any restricted manner will be overtly and specifically defined as such in this Detailed Description section. Both the foregoing general description and the following detailed description are exemplary and explanatory only and are not restrictive of the features, as claimed.

In the detailed description herein, references to "embodiment," "an embodiment," "one non-limiting embodiment," "in various embodiments," etc., indicate that the embodiment(s) described can include a particular feature, structure, or characteristic, but every embodiment might not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

In general, terminology can be understood at least in part from usage in context. For example, terms, such as "and", "or", or "and/or," as used herein can include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, can be used to describe any feature, structure, or characteristic in a singular sense or can be used to describe combinations of features, structures or characteristics in a plural sense. Similarly, terms, such as "a," "an," or "the," again, can be understood to convey a singular usage or to convey a plural usage, depending at least in part upon context. In addition, the term "based on" can be understood as not necessarily intended to convey an exclusive set of factors and can, instead, allow for existence of additional factors not necessarily expressly described, again, depending at least in part on context.

As used herein, the terms "comprises," "comprising," or any other variation thereof are intended to cover a non-exclusive inclusion, such that a process, method, composition, article, or apparatus that comprises a list of elements does not include only those elements, but may include other elements not expressly listed or inherent to such process, method, composition, article, or apparatus. The term "exemplary" is used in the sense of "example" rather than "ideal." As used herein, the singular forms "a," "an," and "the" include plural reference unless the context dictates otherwise. Relative terms such as "about," "substantially," and "approximately" refer to being nearly the same as a referenced number or value, and should be understood to encompass a variation of ±5% of a specified amount or value.

As used herein, a "model" or "machine-learning model" generally encompasses instructions, data, and/or a model configured to receive input, and apply one or more of a weight, bias, classification, or analysis on the input to generate an output. The output may include, for example, a classification of the input, an analysis based on the input, a design, process, prediction, or recommendation associated with the input, or any other suitable type of output. A machine-learning model is generally trained using training data, e.g., experiential data and/or samples of input data, which are fed into the model in order to establish, tune, or modify one or more aspects of the model, e.g., the weights, biases, criteria for forming classifications or clusters, or the like. Aspects of a machine-learning model may operate on an input linearly, in parallel, via a network (e.g., a neural network), or via any suitable configuration.

The execution of the machine-learning model may include deployment of one or more machine learning techniques, such as linear regression, logistical regression, random forest, gradient boosted machine (GBM), deep learning, and/or a deep neural network. Supervised and/or unsupervised training may be employed. For example, supervised learning may include providing training data and labels corresponding to the training data, e.g., as ground truth. Unsupervised approaches may include clustering, classification, or the like. Any suitable type of training may be used, e.g., stochastic, gradient boosted, random seeded, recursive, epoch or batch-based, etc.

Certain non-limiting embodiments are described below with reference to block diagrams and operational illustrations of methods, processes, devices, and apparatus. It is understood that each block of the block diagrams or operational illustrations, and combinations of blocks in the block diagrams or operational illustrations, can be implemented by means of analog or digital hardware and computer program instructions. These computer program instructions can be provided to a processor of a general purpose computer to alter its function as detailed herein, a special purpose computer, ASIC, or other programmable data processing apparatus, such that the instructions, which execute via the processor of the computer or other programmable data processing apparatus, implement the functions/acts specified in the block diagrams or operational block or blocks. In some alternate implementations, the functions/acts noted in the blocks can occur out of the order noted in the operational illustrations. For example, two blocks shown in succession can in fact be executed substantially concurrently, or the blocks can sometimes be executed in the reverse order, depending upon the functionality/acts involved.

Exemplary Environment

FIG. 1 depicts an exemplary environment 100 that may be utilized with techniques presented herein. One or more user device(s) 105, one or more external system(s) 110, one or more server system(s) 115, and one or more provider device(s) 120 may communicate across a network 101. As will be discussed in further detail below, the server system 115 may communicate with one or more of the other components of the environment 100 across network 101. The user device 105 may be associated with a user, such as a patient, e.g., a mental health patient. The provider device 120 may be associated with a healthcare provider, such as a mental health provider, such as a psychiatrist. The provider may be associated with one or more of generating, training, using, or tuning a machine-learning model to analyze user response data to create an assessment recommendation. Additionally, or alternatively, the provider may belong to one or more organizations, where the provider may have one or more accounts for staff, medical and administrative personnel, each with appropriate access to patient data, medication requests, scheduling, and the like.

In some embodiments, the components of the environment 100 are associated with a common entity. In some embodiments, one or more of the components of the environment is associated with a different entity than another. The systems and devices of the environment 100 may communicate in any arrangement. As will be discussed herein, systems and/or devices of the environment 100 may communicate in order to one or more of generate, train, tune, and/or use a machine-learning model to analyze user response data to create an assessment recommendation.

The user device 105 may be configured to enable the user (e.g., patient) to access and/or interact with other systems in the environment 100. For example, the user device 105 may be a computer system such as, for example, a desktop computer, a mobile device, a tablet, a wearable, etc. In some embodiments, the user device 105 may include one or more electronic application(s), e.g., a program, plugin, browser extension, etc., installed on a memory of the user device 105.

The user device 105 may include a display/user interface (UI) 105A, a processor 105B, a memory 105C, and/or a network interface 105D. The user device 105 may execute, by the processor 105B, an operating system (O/S) and at least one electronic application (each stored in memory 105C). The electronic application may be a desktop program, a browser program, a web client, or a mobile application program (which may also be a browser program in a mobile O/S), an applicant specific program, system control software, system monitoring software, software development tools, or the like. For example, environment 100 may extend information on a web client that may be accessed through a web browser. In some embodiments, the electronic application(s) may be associated with one or more of the other components in the environment 100. The application may manage the memory 105C, such as a database, to transmit streaming data to network 101. The display/UI 105A may be a touch screen or a display with other input systems (e.g., mouse, keyboard, etc.) so that the user(s) may interact with the application and/or the O/S. The network interface 105D may be a TCP/IP network interface for, e.g., Ethernet or wireless communications with the network 101. The processor 105B, while executing the application, may generate data and/or receive user inputs from the display/UI 105A and/or receive/transmit messages to the server system 115, and may further perform one or more operations prior to providing an output to the network 101.

The provider device 120 may be configured to enable the provider (e.g., healthcare or mental health professional) to access and/or interact with other systems in the environment 100. For example, the provider device 120 may be a computer system such as, for example, a desktop computer, a mobile device, a tablet, a wearable, etc. In some embodiments, the provider device 120 may include one or more electronic application(s), e.g., a program, plugin, browser extension, etc., installed on a memory of the provider device 120.

The provider device 120 may include a display/user interface (UI) 120A, a processor 120B, a memory 120C, and/or a network interface 120D. The provider device 120 may execute, by the processor 120B, an operating system (O/S) and at least one electronic application (each stored in memory 120C). The electronic application may be a desktop program, a browser program, a web client, or a mobile application program (which may also be a browser program in a mobile O/S), an applicant specific program, system control software, system monitoring software, software development tools, or the like. For example, environment 100 may extend information on a web client that may be accessed through a web browser. In some embodiments, the electronic application(s) may be associated with one or more of the other components in the environment 100. The application may manage the memory 120C, such as a database, to transmit streaming data to network 101. The display/UI 120A may be a touch screen or a display with other input systems (e.g., mouse, keyboard, etc.) so that the user(s) may interact with the application and/or the O/S. The network interface 120D may be a TCP/IP network interface for, e.g., Ethernet or wireless communications with the network 101. The processor 120B, while executing the application, may generate data and/or receive user inputs from the display/UI 120A and/or receive/transmit messages to the server system 115, and may further perform one or more operations prior to providing an output to the network 101.

External systems 110 may be, for example, one or more third party and/or auxiliary systems that integrate and/or communicate with the server system 115 in performing various natural language email instruction tasks. External systems 110 may be in communication with other device(s) or system(s) in the environment 100 over the one or more networks 101. For example, external systems 110 may communicate with the server system 115 via API (application programming interface) access over the one or more networks 101, and also communicate with the user device 105 and/or the provider device 120 via web browser access over the one or more networks 101.

In various embodiments, the network 101 may be a wide area network ("WAN"), a local area network ("LAN"), a personal area network ("PAN"), or the like. In some embodiments, network 101 includes the Internet, and information and data provided between various systems occurs online. "Online" may mean connecting to or accessing source data or information from a location remote from other devices or networks coupled to the Internet. Alternatively, "online" may refer to connecting or accessing a network (wired or wireless) via a mobile communications network or device. The Internet is a worldwide system of computer networks-a network of networks in which a party at one computer or other device connected to the network can obtain information from any other computer and communicate with parties of other computers or devices. The most widely used part of the Internet is the World Wide Web (often-abbreviated "WWW" or called "the Web"). A "website page" generally encompasses a location, data store, or the like that is, for example, hosted and/or operated by a computer system so as to be accessible online, and that may include data configured to cause a program such as a web browser to perform operations such as send, receive, or process data, generate a visual display and/or an interactive interface, or the like.

The server system 115 may include an electronic data system, e.g., a computer-readable memory such as a hard drive, flash drive, disk, etc. In some embodiments, the server system 115 includes and/or interacts with an application programming interface for exchanging data to other systems, e.g., one or more of the other components of the environment.

The server system 115 may include a database 115A and at least one server 115B. The server system 115 may be a computer, system of computers (e.g., rack server(s)), and/or or a cloud service computer system. The server system may store or have access to database 115A (e.g., hosted on a third-party server or in memory 115E). The server(s) may include a display/UI 115C, a processor 115D, a memory 115E, and/or a network interface 115F. The display/UI 115C may be a touch screen or a display with other input systems (e.g., mouse, keyboard, etc.) for an operator of the server 115B to control the functions of the server 115B. The server system 115 may execute, by the processor 115D, an operating system (O/S) and at least one instance of a servlet program (each stored in memory 115E).

The server system 115 may generate, store, train, tune, or use a machine-learning model, configured to analyze user response data to create an assessment recommendation. The server system 115 may include a machine-learning model and/or instructions associated with the machine-learning model, e.g., instructions for generating a machine-learning model, training the machine-learning model, using the machine-learning model, etc. The server system 115 may include instructions for processing natural language user responses, e.g., based on the output of the machine-learning model, and/or operating the display 115C to output an action, e.g., as adjusted based on the machine-learning model. The server system 115 may include training data.

In some embodiments, a system or device other than the server system 115 is used to generate and/or train the machine-learning model. For example, such a system may include instructions for generating the machine-learning model, the training data and ground truth, and/or instructions for training the machine-learning model. A resulting trained machine-learning model may then be provided to the server system 115.

Generally, a machine-learning model includes a set of variables, e.g., nodes, neurons, filters, etc., that are tuned, e.g., weighted or biased, to different values via the application of training data. In supervised learning, e.g., where a ground truth is known for the training data provided, training may proceed by feeding a sample of training data into a model with variables set at initialized values, e.g., at random, based on Gaussian noise, a pre-trained model, or the like. The output may be compared with the ground truth to determine an error, which may then be back-propagated through the model to adjust the values of the variable.

Training may be conducted in any suitable manner, e.g., in batches, and may include any suitable training methodology, e.g., stochastic or non-stochastic gradient descent, gradient boosting, random forest, etc. In some embodiments, a portion of the training data may be withheld during training and/or used to validate the trained machine-learning model, e.g., compare the output of the trained model with the ground truth for that portion of the training data to evaluate an accuracy of the trained model. The training of the machine-learning model may be configured to cause the machine-learning model to learn associations between the user questions, user response data, and user data, such that the trained machine-learning model is configured to create an assessment recommendation.

In various embodiments, the variables of a machine-learning model may be interrelated in any suitable arrangement in order to generate the output. For example, the machine-learning model may include one or more convolutional neural networks ("CNN") and may include further architecture, e.g., a connected layer, neural network, etc., configured to determine a relationship between the identified features in order to create an assessment recommendation.

Further aspects of the machine-learning model and/or how it may be utilized to process user response data in further detail in the method below. In the following methods, various acts may be described as performed or executed by a component from FIG. 1, such as the server system 115, the user device 105, the provider device 120, or components thereof. However, it should be understood that in various embodiments, various components of the environment 100 discussed below may execute instructions or perform acts including the acts discussed below. An act performed by a device may be considered to be performed by a processor, actuator, or the like associated with that device. Further, it should be understood that in various embodiments, various steps may be added, omitted, and/or rearranged in any suitable manner.

Figure 2:
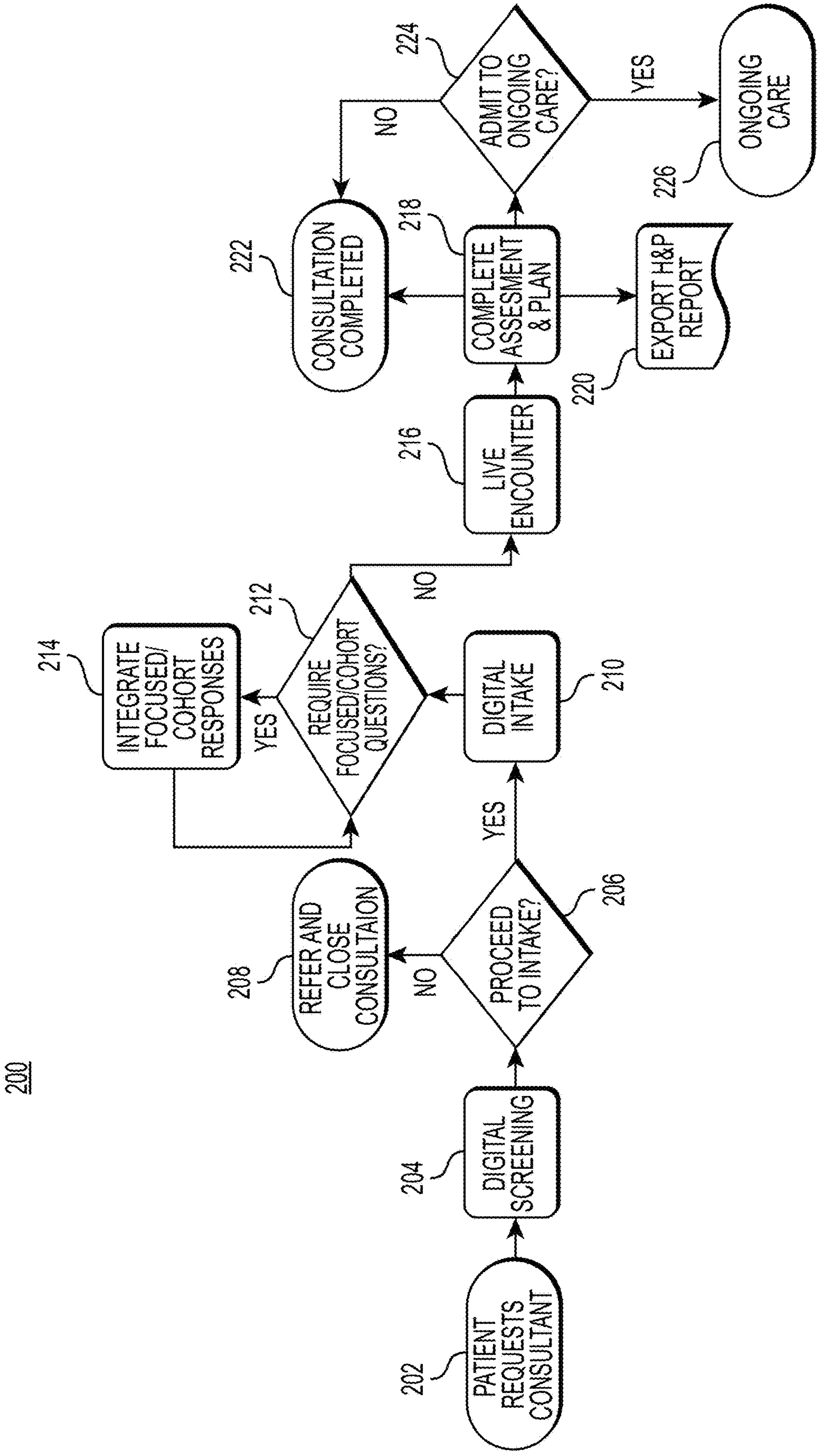
FIG. 2 depicts a flowchart of an exemplary process for a mental health user assessment, according to one or more embodiments.
Figure 3A:
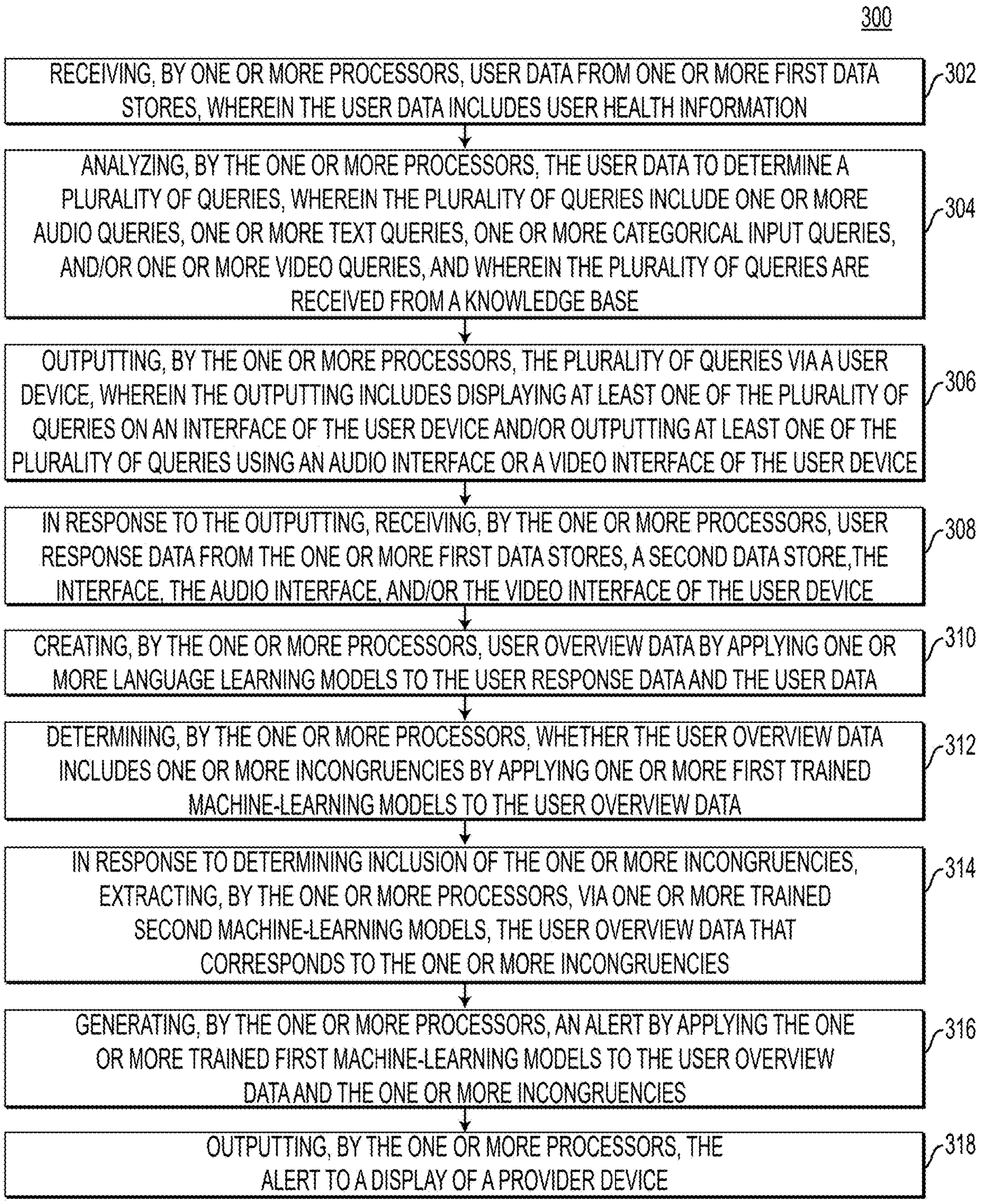
FIG. 3A depicts a flowchart of an exemplary method for utilizing a health control system, according to one or more embodiments.
Figure 3B:
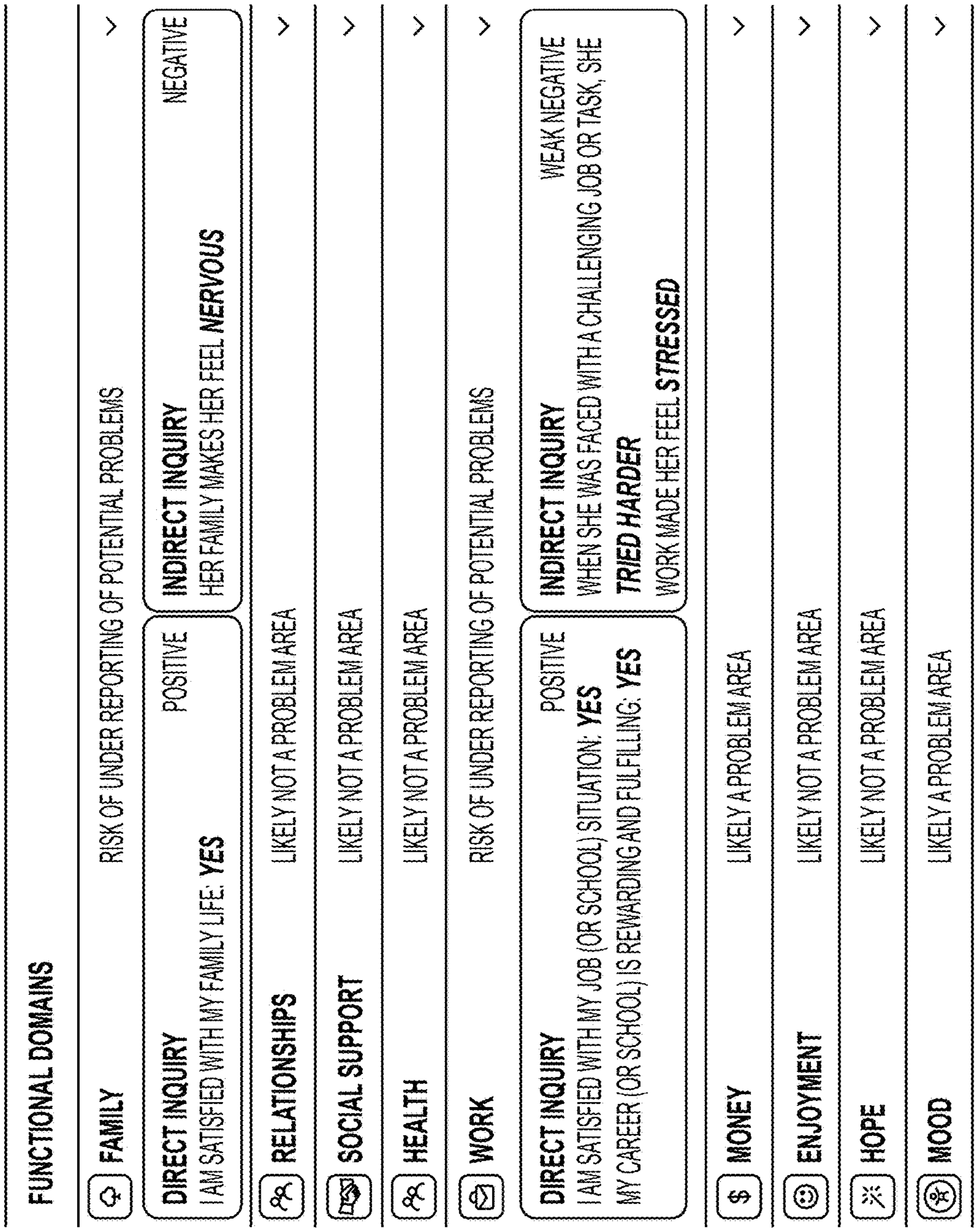
FIG. 3B depicts an exemplary dashboard that includes one or more functional domains, according to one or more embodiments.
Figure 3C:
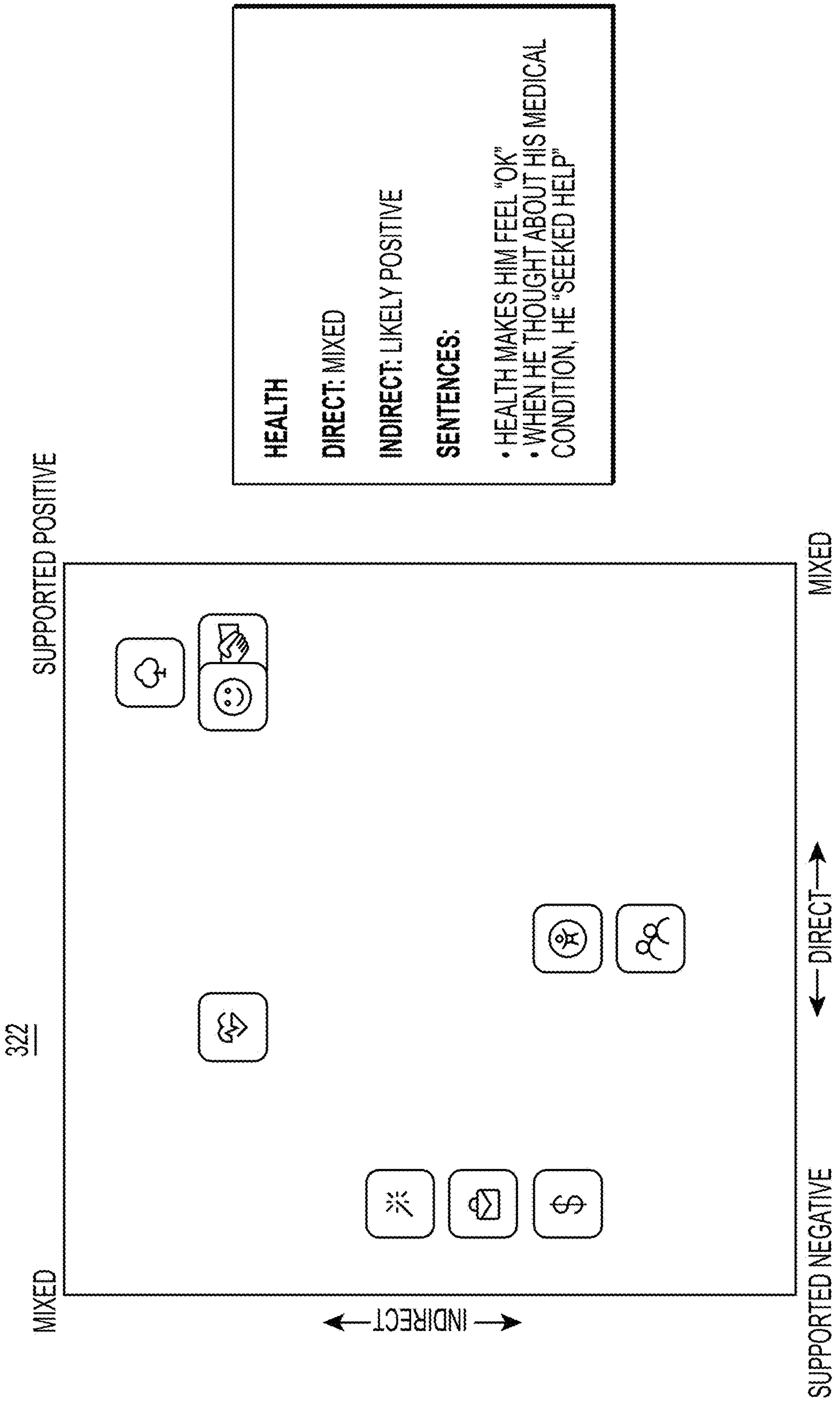
FIG. 3C depicts an exemplary prototypical example, according to one or more embodiments.
Figure 3D:
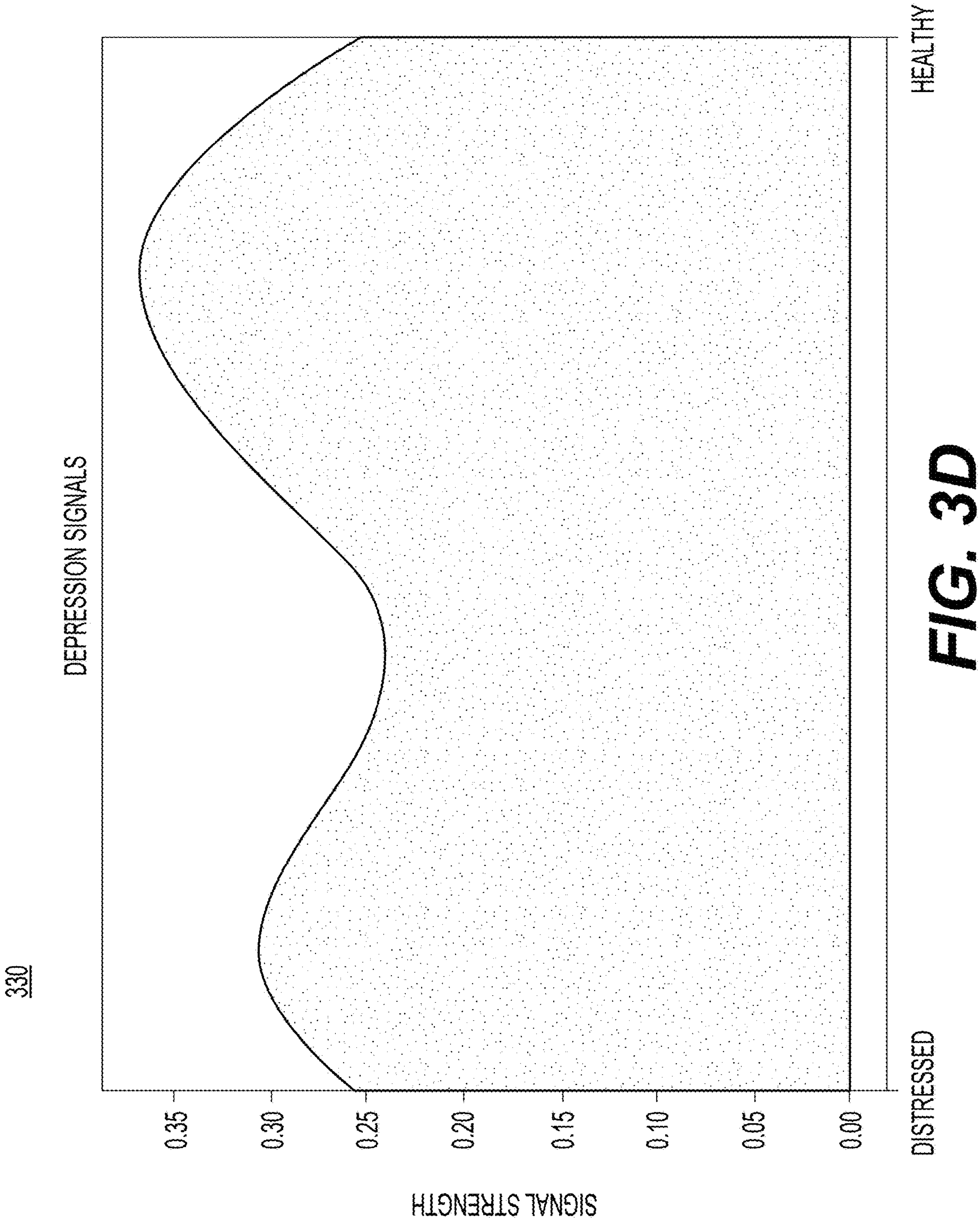
FIG. 3D depicts an exemplary visualization plot, according to one or more embodiments.
Figure 3E:
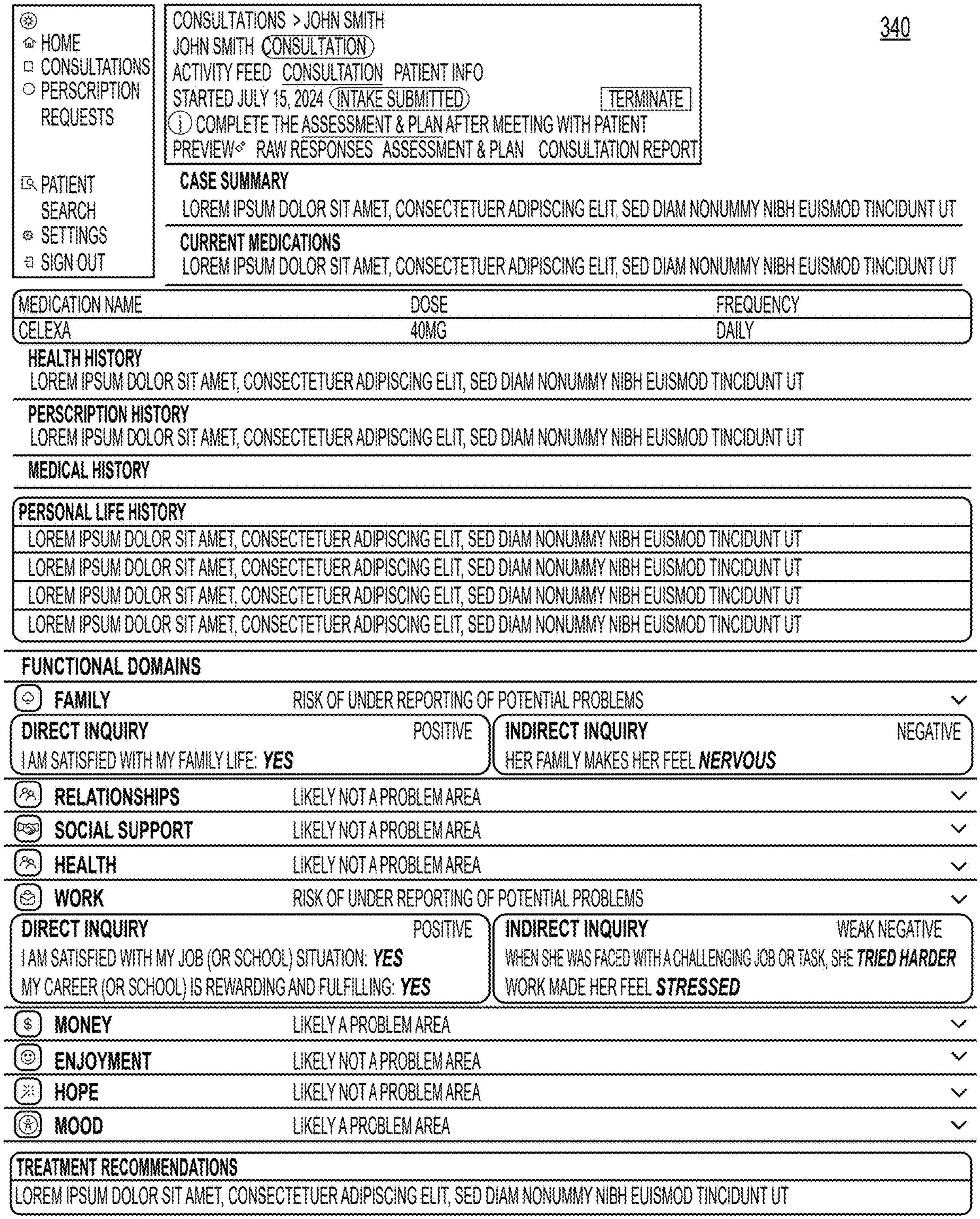
FIG. 3E depicts an exemplary user dashboard, according to one or more embodiments.
Figure 3E:
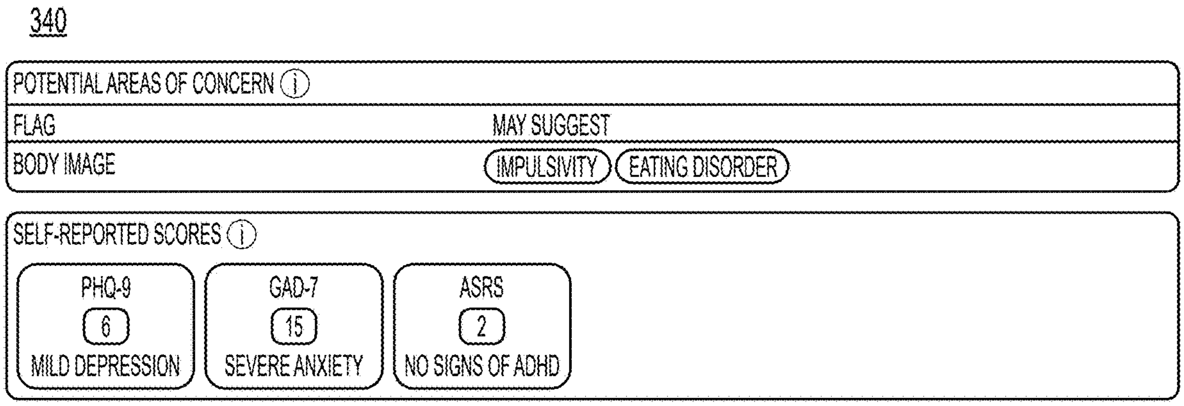
Figure 3F:
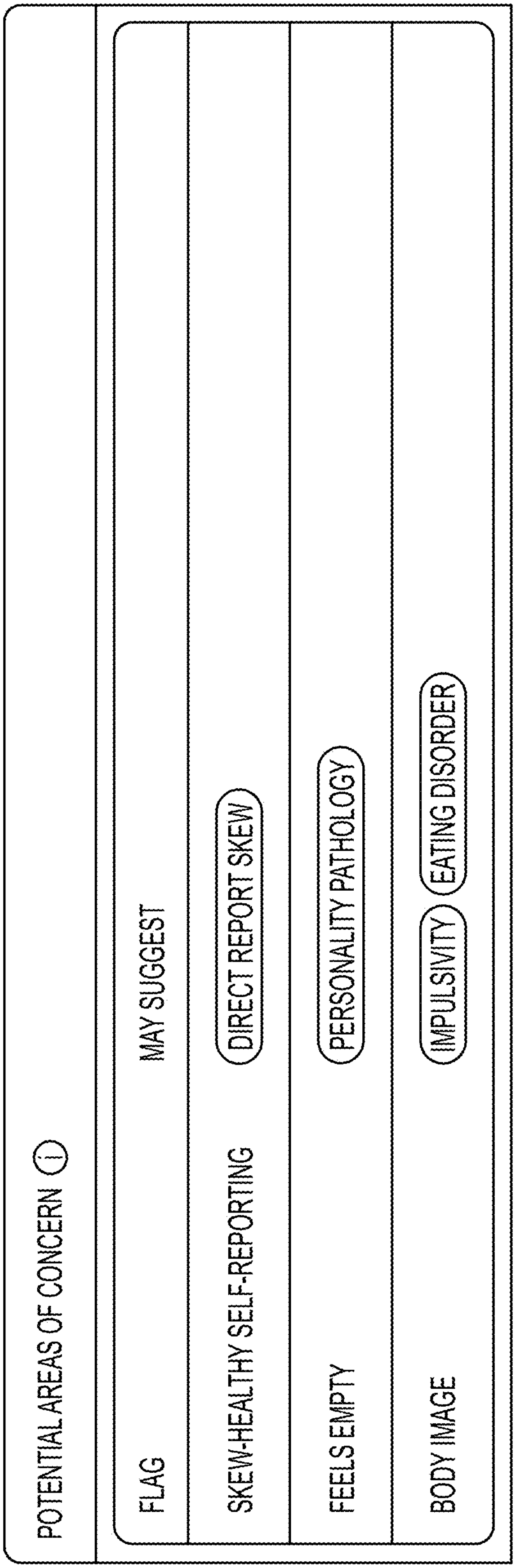
FIG. 3F depicts an exemplary user interface that indicates potential areas of concern, according to one or more embodiments.
Figure 4:
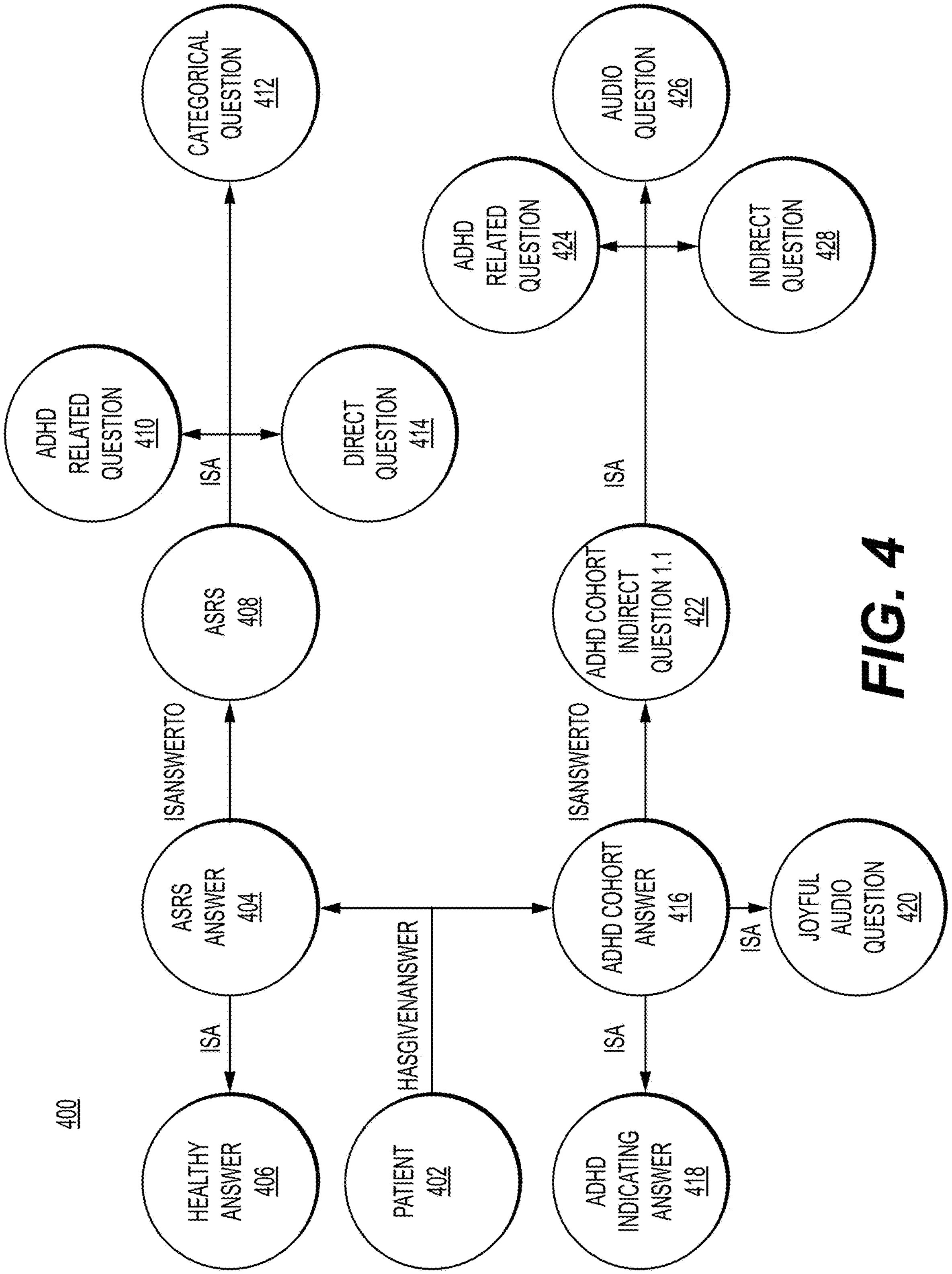
FIG. 4 illustrates an exemplary graph that outlines exemplary user response relationships, according to one or more embodiments.

In general, any process or operation discussed in this disclosure that is understood to be computer-implementable, such as the process illustrated in FIGS. 2-4, may be performed by one or more processors of a computer system, such as any of the systems or devices in the environment 100 of FIG. 1, as described above. A process or process step performed by one or more processors may also be referred to as an operation. The one or more processors may be configured to perform such processes by having access to instructions (e.g., software or computer-readable code) that, when executed by the one or more processors, cause the one or more processors to perform the processes. The instructions may be stored in a memory of the computer system. A processor may be a central processing unit (CPU), a graphics processing unit (GPU), or any suitable types of processing unit.

A computer system, such as a system or device implementing a process or operation in the examples below, may include one or more computing devices, such as one or more of the systems or devices in FIG. 1. One or more processors of a computer system may be included in a single computing device or distributed among a plurality of computing devices. A memory of the computer system may include the respective memory of each computing device of the plurality of computing devices.

Although depicted as separate components in FIG. 1, it should be understood that a component or portion of a component in the environment 100 may, in some embodiments, be integrated with or incorporated into one or more other components. For example, a portion of the display 115C may be integrated into the user device 105 or the like. In some embodiments, operations or aspects of one or more of the components discussed above may be distributed amongst one or more other components. Any suitable arrangement and/or integration of the various systems and devices of the environment 100 may be used.

Exemplary Process for Utilizing a Health Control System

FIG. 2 depicts a flowchart of an exemplary process 200 for a mental health user assessment, according to one or more embodiments. Process 200 may be performed by one or more processors of a server (e.g., server system 115) that is in communication with one or more user devices (e.g., user device 105), one or more provider devices (e.g., provider device 120), and other external system(s) (e.g., server system 115) via a network (e.g., network 101). However, it should be noted that process 200 may be performed by any one or more of the server, one or more user devices, or other external systems.

The process may first begin with a user requesting a consultation (e.g., logging on a mobile application of a user device) (Step 202). For example, the user may log on to the mobile application, request a consultation, and then the user may be prompted to enter some initial user information (e.g., address, phone number).

The process may include performing an initial digital screening (Step 204). The initial digital screening may aid providers in screening (e.g., conducting an initial analysis) of users (e.g., patients). The system may display one or more queries to the user, where the user may prove a response to the system (e.g., via text, video, pictures). The provider may analyze the user response data and determine whether the process should continue with an intake consultation, or refer the user to other providers and/or external stakeholders.

The initial digital screening may include queries that have been ordered into a plurality of sections or a plurality of query types. The queries may be output (e.g., displayed) to the user, where the user may provide a response to the system. In one example, the initial digital screening may be ordered into seven sections, which may include: (1) How can I help? (2) Getting to know you; (3) Your health story; (4) Adult ADHD Self-Report Scale (ASRS); (5) Patient Health Questionnaire-9 (PHQ9); (6) General Anxiety Disorder-7 (GAD7); and (7) More about you. The initial screening may be performed by analyzing the user's data in view of assessment parameters. Exemplary Table 1 below outlines eleven exemplary assessment parameters, although any number or combination of assessment parameters may be used. The assessment parameters may be displayed using one or more modalities (e.g., string, audio (mp3), video), and the assessment parameter responses may be received using one or more modalities. Additionally, although certain assessment parameters may be described below in terms of receiving information via free text, multiple choice, audio, video, etc., it is recognized that any assessment parameter may be received via any suitable format.

TABLE 1

User Initial Screening parameters

| No | Input parameters | Description | Data modality | Format |
|---|---|---|---|---|
| 1 | Age | Patient's age | numeric | integer |
| 2 | Sex | Male, Female, Other | | |
| 3 | Seeking care motivation | The patient describes which person or issue is the primary motivation for seeking care. Multiple choice. | numeric | integer |
| 4 | Current therapist | Patient declares if he/she currently sees a therapist | text | binary (Y/N) |
| 5 | Past therapist | Have you ever seen a therapist in the past? | text | binary (Y/N) |
| 6 | Mind-body questions | Patient answers questions relating to self-awareness and mind-body | text | Binary (Y/N) |
| 7 | Medical Issues | Patient declares any medical issues | text | string |
| 8 | Current medication | List of medication the patient is currently taking (Name, dose, frequency) | text, numeric | string, integer/ float |
| 9 | Chief complaint | Patient describes why he/she needs assistance | audio/Text | mp3/string |
| 10 | Self-report ADHD test | ASRS - Part A, 6 multiple questions (Never, Rarely, Sometimes, Often, Very often) | numeric | integer |
| 11 | PHQ-9 | 9 questions | numeric | integer/ float |
| 12 | GAD-7 | To identify probable cases of Generalized Anxiety Disorder (GAD) and assess symptom severity in GAD | numeric | integer/ float |
| 13 | Treatment history | Whether or not the patient has a history of psychiatric treatment, hospitalizations, and/or medication | numeric | binary |
| 14 | Personal life | Relationship status, employment status and description, who is living at home | Numeric | integer |
| 15 | SIP | A set of true false questions aimed at detecting signs of Substance use, Impulsivity and Personality disorders (SIP) | Numeric | binary |

The above table is exemplary only and the exact language used may differ, the order in which information is sought may differ, and other prompts/outputs or combinations of prompts/outputs may be used.

The age parameter may correspond to the user's age. The sex parameter may correspond to the user's sex. The seeking care motivation parameter may correspond to which person and/or issue is the primary motivation for seeking care. The seeking care motivation may include a multiple choice option. For example, the seeking care motivation may include one or more of the following options: (1) I am personally motivated to seek care; (2) A family member or friend is encouraging me to seek care; (3) A work or legal issue is prompting me to seek care; and/or (4) Another reason (please specify if comfortable-free text). In other aspects, the seeking care motivation response may be input by the user via free text. The current therapist parameter may correspond to the user indicating if he/she/they currently see a therapist. Additionally, for example, if the user indicates that the user is currently seeing a therapist, the system may request the following information: therapist name, therapist contact information (e.g., address, phone number), and/or permission for contacting the therapist (e.g., information release). Additionally, or alternatively, the system may ask the user if the user has seen a therapist in the past. In some aspects, the answer to an initial question may affect the next question, or the type of input a user is allowed to give in response (e.g., Y/N versus free text versus multiple choice). As an example, the system may output a question to the user regarding whether the user has seen a psychiatrist in the past in the form of a Y/N question. If the user answers 'yes,' then an additional free text question may be asked of the user. For example, the user may be asked whether they have been hospitalized for psychiatric reasons in the past or whether they have taken psychiatric medications in the past. In some aspects, the answer provided by a user during an initial digital screening may affect questions asked during a later intake evaluation. For example, if a user indicated they had seen a psychiatrist in the past on the initial screening, the user may be asked further questions regarding interactions with a psychiatrist in the past on the subsequent intake assessment, without being asked again whether the user has seen a psychiatrist in the past.

In some aspects, a user may be asked questions relating to self-awareness and mind-body. For example, the system may output one or more of the following questions: (1) Have you experienced physical symptoms that: a) are sudden and you do not understand? (Y/N), b) are enduring or persistent and you do not understand? (Y/N), c) you fear? (Y/N); (2) do you feel like you are living in alignment with how you wish to be living (Likert scale: 0 (not at all) to 5 (completely)); and/or (3) How open are you learning new information about how to use your body's clues to resolve symptoms and get better psychologically? (Likert scale: 0 (not at all) to 5 (completely)). The medical issues parameter may correspond to any medical issues declared by the user. The current medication parameter may correspond to a user provided list of medications that the user is currently taking. Additionally, for example, if the user is taking a medication, the current medication parameter may also include a medicine name, a medicine dose, and/or a medicine frequency. The chief complaint parameter may correspond to the user's description of assistance may be needed (e.g., a chief complaint). For example, the system may ask the user the following: Please tell me what is going on and how we can I help?

The substance, impulsivity, personality and/or pathology (SIP) parameter may correspond to the user's substance use, impulsivity (e.g., acting out, dangerous things, overindulgence, angry, violent, rage, bipolar links, uncontrolled compulsive behaviors, and/or suicide ideation or attempts), and/or personality pathology (e.g., empty, pattern repetition of relationship dysfunction/repeated failures in relationships, addicted to love-lost when it is not there, attention seeker, misunderstood, feeling not understood, alone, abandoned, mistreated, left out, not belonging). For example, the system may present one or more of the following yes or no questions and/or statements: 1) Have you ever shaded the truth to get out of a difficult situation? (Validity); 2) My drug use gets me into trouble (Substances); 3) I drink too much (Substances, Alcohol); 4) No matter what I do or who I am with, I feel empty (Personality); 5) People always leave me, and I don't know why (Personality); 6) Sometimes I harm myself to relieve tension (Impulsivity, Personality); 7) My friends think I drink too much or use too many drugs (Substances); 8) I get enraged when people disappoint me (Personality); 9) People have told me that I do dangerous things (Impulsivity); 10) My attitude towards food is worrisome (Impulsivity); and/or 11) No matter what people say, I don't like the way my body looks (Impulsivity). In one or more of the described questions, if the answer is "Yes," the answer may be indicative of a potential pathological problem (interpersonal issues) that may affect risk stratification regarding substance use, impulsivity, and/or personality pathology.

The Self-Report ADHD Test parameter may correspond to whether the system identifies the user as a potential ADHD user. In some embodiments, the Self-Report ADHD Test parameter may be based on the Adult ADHD Self-Report Scale Symptom Checklist (ASRS). The ASRS may include a self-reported questionnaire used to assist in the diagnosis of adult ADHD.

The User (e.g., patient) Health Questionnaire-9 (PHQ-9) parameter may correspond to a self-administered diagnostic tool for assessing and monitoring depression severity. For example, the questionnaire may include nine questions, each relating to a symptom of depression as outlined in the Diagnostic and Statistical Manual of Mental Disorders (DSM-IV). The nine questions may include nine sub-questions to the initial question of: "Over the last 2 weeks, how often have you been bothered by any of the following problems? (Not at all, Several days, More than half the days, Nearly every day)." The nine sub-questions may include one or more of the following: (1) Little interest or pleasure in doing things; (2) Feeling down, depressed, or hopeless; (3) Trouble falling or staying asleep, or sleeping too much; (4) Feeling tired or having little energy; (5) Poor appetite or overeating; (6) Feeling bad about yourself—or that you are a failure or have let yourself or your family down; (7) Trouble concentrating on things, such as reading the newspaper or watching television; (8) Moving or speaking so slowly that other people could have noticed? Or the opposite—being so fidgety or restless that you have been moving around a lot more than usual; and/or (9) Thoughts that you would be better off dead or of hurting yourself in some way.

The General Anxiety Disorder 7-Item Scale (GAD-7) may correspond to whether the user has anxiety and/or the severity of the user's anxiety.

The treatment history parameter may correspond to answers to the following three questions: (1) I have seen a psychiatrist in the past (Y/N); (2) I have been hospitalized for psychiatric reasons in the past (Y/N); and/or (3) I have taken psychiatric medications in the past (Y/N). If the user answers "yes" to the first question, and the patient continues to the intake assessment, an additional free text question may be displayed to the patent on the intake (without asking again whether they have seen a psychiatrist in the past). Additionally, or alternatively, if the user answers "yes" to the third question, and the patient continues to the intake assessment, the system may display additional free text questions regarding the psychiatric medications may be given to the user (e.g., patient) on the intake.

In some embodiments, the initial screening may include collecting user data, such as the user's information (e.g., user name, user email, user address, user number, user identifier, and/or user emergency contact information), the user's primary care physician information (e.g., primary care name, primary care email, and/or primary care number), health insurance information, and/or the user's desired pronoun (e.g., his, her, they). Additionally, or alternatively, the provider may also provide or be prompted to provide alternative or additional user data to the system.

The process may include determining whether to proceed to an intake consultation (Step 206) based on the results of the initial screening or whether to refer the user to other providers or external stakeholders and close the consultation (Step 208). For example, the provider may analyze response data from the initial screening to determine whether to proceed with an intake consultation. The purpose of the digital screening (Step 204) may be to offer the provider additional information regarding determining whether to proceed to the intake (Step 206) or whether to refer the user to other providers or external stakeholders and close the consultation (Step 208). The digital intake (Step 210) may be based on a plurality of intake consultation parameters, for example, all or a subset of the twelve exemplary intake consultation parameters listed below in exemplary Table 2. Depending on the results of the intake consultation, the process may include determining whether to proceed to an ongoing live assessment (Step 212). For example, the provider may analyze the results of the intake consultation to determine whether to proceed with an ongoing live assessment.

In some embodiments, after step 210, the process may include determining whether to ask the user focused questions (e.g., focused refining query) or and/or cohort questions (Step 212). Upon asking the user one or more focused questions and/or one or more cohort questions, the system may integrate the user's responses in the summary data (described below) and/or other user data (e.g., stored in a database) (Step 214).

For example, a focused refining query may include one or more of the following criteria: (1) the focused refining query may be specific and personalized so that it would not make sense to add the focused refining query to the intake; (2) the focused refining query may include an empathetic tone; and/or (3) the focused refining query may serve a clear purpose such that a user's response would include useful information for the provider.

The focused refining queries may relate to different areas of interest, where the areas of interest may be organized into a plurality of different layers. In one embodiment, the queries may be organized into at least one of three areas of interest (e.g., layers). The three areas may include: (1) a history of present illness and a corresponding timeline (e.g., related to elucidating symptom quality, quantity, timing, duration, associated manifestations, aggravating and alleviating factors, for the main self-reported symptoms by the patient); (2) one or more functional domains and daily life data (e.g., related to functional domains (Family, Relationships, Social Support, Health, Work, Money, Enjoyment, Mood, Hope)), and/or (3) core character, associations, and the subconscious (e.g., related to the user's unconscious self, elements of which can be uncovered via indirect and projective questions). The one or more functional domains and daily life data may include the following priority: (1) incongruous or inconsistent domains (e.g., when incongruities or inconsistencies are present, clarifying questions may be asked to try to better understand the user story relating to this domain); (2) negative domains (e.g., problematic domains that are likely linked to the present illness, where clarifying questions might help the provider's understanding); (3) positive domains (e.g., positive domains that may be useful therapeutically).

For example, a focused refining query may include one or more of the following criteria: (1) the focused refining query may be specific and personalized so that it would not make sense to add the focused refining query to the intake; (2) the focused refining query may include an empathetic tone; and/or (3) the focused refining query may include a clear purpose that a user's response would include useful information for the provider. For example, the cohorts may include an anxiety cohort, a depression cohort, an addiction cohort, an obsessive-compulsive disorder cohort, a post-traumatic stress cohort, an ADHD cohort, and/or a post-partum/peri-partum cohort, or any other suitable cohort type, which may or may not correlate to a general category of diagnosis or potential diagnosis. In some embodiments, if the system determines that the user might belong to an ADHD cohort, the provider may determine whether to order an ADHD flow. The anxiety cohort may include users who face anxiety based on medication (e.g., antidepressants, benzodiazepines), complaints (e.g., audio data, video data) from the initial screening, GAD-7 results from the initial screening, and/or a primary issue reported by the provider (e.g., for existing users). The depression cohort may include users who face depression based on medication (e.g., antidepressants, benzodiazepines), complaints (e.g., audio data, video data), and/or a primary issue reported by the provider. The ADHD cohort may be based on a user's responses to indirect ADHD questions (e.g., describe how the morning looks when you are leaving the house, describe your daily work lunch plan), and/or childhood related questions (e.g., What patterns of behavior were noted in your report cards? What was the morning like before school?). Depending on the responses provided during the intake consultation, a user may be assigned to a cohort, and different work flows may be initiated. A work flow for a given cohort may include eliciting information from the user that would be appropriate for the given disorder or complaints that the user is indicated as potentially having.

Based on the answers users gave during the screening on the six ASRS questions and on the audio chief complaint, a provider may receive a first indication of whether a user may belong to an ADHD cohort. If a provider has decided that a user can proceed to the intake consultation, the user may be able to choose to order the additional ADHD flow questions to form a better assessment. For example, a button labeled "Order ADHD Flow" may be shown under displayed ADHD insights (these are the sentence similarity samples from the patient), and then in the main decision button, if the provider decides to propose to the patient to proceed, a reminder may be displayed (e.g., "you selected to propose to the patient to proceed with the intake and ordered the ADHD flow").

In some embodiments, if the system determines that the user might belong to a post-partum/peri-partum cohort, the provider may determine whether to order an order postpartum/peri-partum women flow. For example, the system may filter the users based on the users that have given birth (e.g., in the past year) and users that may be pregnant. Additionally, based on the filtering, the system may request additional information. The additional information may be collected from one or more of the following questions: 1) Have you ever experienced depression in previous pregnancies? (free text); 2) Edinburgh Postnatal Depression Scale (EPDS) (e.g., 10 questions (attention to the last question) Total <10); and/or 3) Thematic Apperception Test (TAT, indirect stimulus).

For example, TAT may correspond to a projective test that focuses on the subconscious dynamics of a user's personality. The system may prompt the user to describe a picture (example for this cohort is a picture of a mother and a baby) through the following one or more questions: 1) Please tell us a story with a beginning, a middle and an end to this picture; and/or 2) Look at the picture, tell us what's going on, what are the characters thinking and feeling, what led up to this and how it is going to turn out.

In some embodiments, after the digital intake has completed, but before the provider meets the user for the first time, the system may recommend a set of focused refining queries (e.g., questions) that the patient should receive and answer prior to interacting with the provider. The focused refining queries may assist the provider in focusing on specific areas of the user's story (e.g., identified in the intake/screening data) that might be missing or incomplete, in order to increase the efficiency of the process.

The outcome of Step 212 may result in an output that the user should continue with a live assessment with the current provider (Step 216). In addition to the intake consultation parameters, the digital intake consultation may include provider inputs (e.g., provider notes, results of a mental status exam, an initial diagnosis, and/or a plan of care). The digital intake consultation may include one or more of the following sections: (1) Where your story begins, (2) What are you experiencing? (3) Your health story, (4) The people in your life, (5) Education/work/leisure, and/or (6) Associations. Although not specifically described above, the initial digital screening 204 may also or alternatively include provider inputs (e.g., provider notes, results of a mental status exam, an initial diagnosis, and/or a plan of care).

The intake consultation parameters (otherwise referred to as user intake assessment parameters in Table 2 below) may be displayed using one or more modalities (e.g., string, audio (mp3), video), and the intake consultation parameter responses may be received using one or more modalities. It is noted that any combination of consultation parameters described below, or other consultation parameters not shown below, may be used in methods of the embodiment described herein. Additionally, although certain consultation parameters may be described below in terms of receiving information via free text, multiple choice, audio, video, etc., it is recognized that any consultation parameter may be received via any suitable format.

TABLE 2

User Intake Assessment Parameters

| No | Input parameters | Description | Data modality | Format |
|---|---|---|---|---|
| 1 | Earliest Memory | The user's earliest memory | audio | mp3 |
| 2 | Primary Psychiatric Symptoms | Identify primary psychiatric symptoms | text, numeric | string, integer |
| 3 | Psychotic Symptoms | Identify psychotic symptoms | numeric | |
| 4 | Dissociative Symptoms | Identify symptoms that are consistent with dissociation (when users lose time or feel or move from their body) | text, numeric | string, integer |
| 5 | Treatment History | Prior therapists, prior psychiatrists, psychiatric medications, past genetic history, hospitalizations, other outpatient programs | text, numeric | string, integer |
| 6 | Medical History | Medication Allergies, Current Medication, Medical Issues (9 subcategories), past abnormal EKGs, heart murmurs, heart arrhythmia | text, numeric | string, integer |
| 7 | Substance History | Alcohol, marijuana, cocaine, ecstasy/mdma, amphetamines, opioids, smoking, gamble, sexual thoughts | text, numeric | string, integer |
| 8 | Personal History | Childhood, Parental marital status, lives at home, relationship status, children, relationship stresses, occupation, jobs, occupational stresses, sexual issues | audio, numeric | string, integer |
| 9 | Education History | College, Graduate, High School, Grade school (teachers) | text, numeric | string, integer |
| 10 | Family History | Mood disorders, anxiety disorders, addiction disorders, ADHD, suicide attempts/completed/ mysterious deaths, sudden deaths at young age while playing sports | text, numeric | string, integer |
| 11 | Functional Domain Assessment | Assessment of the user functional domains based on 7 multiple choice questions (linked with SCT) | numeric | integer |
| 12 | SCT | Sentence Completion Test | text | string |

The above Table 2 is exemplary only and the exact language used may differ, the order in which information is sought may differ, and other prompts/outputs or combinations of prompts/outputs may be used.

The Earliest Memory parameter may correspond to the user's earliest memory (e.g., when a user thinks of a memory currently and/or how the user feels within the memory). For example, the system may ask the users one or more of the following questions: Take a minute to think about the people that may be in your memory, who are they and who do you think about when you think of these people? Sometimes memories occur in distinctive places, What do you recall about the place(s) in your memory? Take a minute and discuss. Often times there are distinct objects or things in memories. What do you think about as you remember these things?

The Primary Psychiatric Symptom parameter may correspond to the psychiatric symptoms that the user may be experiencing or may have recently experienced. The Psychotic Symptom parameter may correspond to the psychotic symptoms that the user may be experiencing or may have recently experienced. The Dissociative Symptoms parameter may correspond to dissociative symptoms that the user may be experiencing. The Treatment History parameter may correspond to whether the user has seen prior therapists, psychiatrists, whether the user has taken psychiatric medications, whether the user has a past history of genetic testing, whether the user has been medically or psychiatrically hospitalized, and/or whether the user has participated in other outpatient programs or treatments. The Medical History parameter may correspond to the user's medication allergies, medical issues, and the like. The Substance History parameter may correspond to information about the user's history with caffeine, cigarettes, tobacco products, vaporizers, alcohol, marijuana, cocaine, and the like. The Personal History parameter may correspond to information about the user's early life. The Education History parameter may correspond to information about the user's education history. The Family History parameter may correspond to information about the user's family history.

The Functional Domain Assessment parameter may correspond to the user's responses (e.g., Yes, No, N/A) to at least one of the following statements, where one or more machine-learning models may analyze one or more responses to the statements to determine a score, where the score may be used for quantitative analysis, graphic, charting, and the like: (1) I am satisfied with my family life; (2) My relationship with my partner/spouse is fulfilling; (3) I have enough money to meet my needs; (4) I am satisfied with my job (or school) situation; (5) I find it easy to find enjoyable and relaxing activities; (6) I am in good physical health; (7) There are people I can turn to if I need help; (8) Have you ever told a lie? (9) I feel all alone in the world; (10) I have no major health worries; (11) I don't worry about finances; (12) My career (or school) is rewarding and fulfilling; (13) I know how to have fun; (14) I feel optimistic about my future; (15) I have always looked forward to becoming a mother (for post-partum); and/or (16) Motherhood fills me with joy (for post-partum). The system may ask one or more of the following questions: Who would you identify as a hero to you? You can choose anyone from your personal life or even a historical or contemporary figure. Please describe why you consider this person to be a hero. Please tell me someone you regard as a villain or the opposite of a hero and why? The Sentence Completion Test (SCT) parameter may correspond to a user's completion of certain sentences or phrases. Examples of incomplete sentences for the user to complete may include one or more of the following sentences:

Relationship: His/her spouse/partner is . . .
Family: Her family makes her feel . . .
Work and Money: When he/she thought about finances, he/she . . .
Work: Work made him/her feel . . .
Enjoyment: What he enjoyed most was . . .
Health: Health makes him feel . . .
Postpartum: When she held her baby, she . . .
Hope: She feels her future is . . .
Money: Money makes him/her feel . . .
Job Task: When he/she was faced with a challenging job task, he/she . . .
Loneliness: When he/she felt lonely, he/she . . .
Friends: When he/she thought about his/her friends, he/she . . .
Relaxation: To relax he/she . . .
Medical Condition: When he/she thought about his/her medical condition, he/she . . .
Motherhood: Being a mother is . . .
Feeling: Most of the time he/she feels . . .
Impact: Whatever he/she does, he/she feels . . . .

Different categories of sentences or phrases, or different specific examples of sentences of phrases within a given category may be used. Based on the intake assessment, the provider may decide to refer the user to other providers and/or external stakeholders. The raw responses (e.g., raw data) acquired during the digital screening, the intake, and/or the ongoing assessment may be displayed in a dedicated dashboard for explainability purposes so that providers have visibility of the actual user responses. Visualizations of these raw responses may be shown in the exemplary dashboard. Additionally, or alternatively, raw responses may be displayed with the capability for providers to annotate and/or label specific emotions within the audio. For example, one or more machine-learning models may annotate the raw responses to indicate relationships between the data (e.g., showing data is related to certain categories of information). The machine-learning models may update the raw responses to include links and/or labels that indicate support for the functional domain analysis, contraindications, support for the generated summaries, and the like. The machine-learning models may also be configured to fix transcription errors and/or spelling mistakes in the data. In some embodiments, interpretations, quantifications, and/or synthesis of the raw data may also be displayed via the dashboard. For example, as discussed herein, one or more machine-learning models may analyze and synthesize the raw data to generate one or more summaries based on the raw data. The dashboard may display such summaries via the dashboard.

The process may continue with a regular ongoing live assessment of the user (Step 216). During the live assessment, the provider may make decisions regarding what should happen next. However, the ongoing assessment may include the system monitoring raw or processed user data in a variety of ways to aid the providers in having a high frequency overview of the user's well-being. For example, the system may prompt the user to provide various forms of personal health information (PHI) at a frequency determined by the provider and/or the provider may provide inputs. For example, exemplary Table 3 includes seven exemplary assessment parameters, although more or fewer parameters may be used.

TABLE 3

User Ongoing Assessment Parameters

| No | Input parameters | Description | Data modality | Format |
|---|---|---|---|---|
| 1 | Check-ins | User records an audio check-in | audio | mp3 |
| 2 | Progress reporting | User reports "How would you describe your emotional status since you last reported?". Multiple choice: improved, same, worse | numeric | integer |

TABLE 3-continued

User Ongoing Assessment Parameters

| No | Input parameters | Description | Data modality | Format |
|---|---|---|---|---|
| 3 | PHQ-9 | User fills the PHQ-9 | numeric | integer |
| 4 | GAD-7 | User fills the GAD-7 | numeric | integer |
| 5 | Sleep data | Sleep data are acquired from wearables, e.g., the Oura rings, Apple watch, fitness trackers, etc. | numeric | integer |
| 6 | Functional Domain Assessment | Assessment of the user functional domains based on 7 multiple choice questions (linked with Sentence Completion Test) | numeric | integer |
| 7 | SCT | Sentence Completion Test | text | string |
| 8 | TAT Cards | Thematic apperception test cards | text or audio | string or mp3 |
| 9 | Focused Questions | System generated questions | text or audio | string or mp3 |
| 10 | Earliest Memory | Questions about a user's earliest memory | text or audio | string or mp3 |

The above table is exemplary only and the exact language used may differ, the order in which information is sought may differ, and other prompts/outputs or combinations of prompts/outputs may be used.

The Check-ins assessment parameter may correspond to a user audio record, where the user describes how the user is doing, whether in response to questions, prompts, or an ongoing dialogue, etc. The Progress Reporting assessment parameter may correspond to information regarding the user's emotional state (e.g., "How would you describe your emotional status since you last reported?"). The PHQ-9 and the GAD-7 have been described above. The Sleep Data assessment parameter may correspond to the user's sleep data. In some embodiments, the user's sleep data may be collected by one or more sensors, e.g., by one or more wearable devices. The Functional Domain Assessment parameter and the SCT parameters have been described above. It is noted that any combination of ongoing assessment parameters described, or other ongoing assessment parameters not shown, may be used in methods of the embodiment described herein. The TAT cards assessment parameter may correspond to "Thematic apperception test" cards that may include projective tests, where a user may be shown an image and may be asked to come up with a story with a beginning, a middle, and an end. The system may recommend the TAT cards to the provider, or the TAT cards might be ordered by the provider without a recommendation. The recommendation criteria may correspond to a self-report incongruity, or on missing/sparse information. For example, if the system detects an incongruity in the "Work" domain, a specific TAT card might be recommended to elucidate the user's functioning within the domain. The focused questions assessment parameter might correspond to one or more system generated questions that are recommended to the provider. The focused questions may take historical information into account to provide context, where the historical information may have been gathered via the ongoing care assessments. Such information may be displayed in the provider's dashboard, where the focused questions may be updated based on new information. The provider may decide whether to ask the focused question to the user. The earliest memory assessment parameter may correspond to a set of questions regarding the user's earliest memory from the intake, what is the earliest memory, how the user feels within the memory, how the user feels about the memory now, and/or what the user thinks of people, places, and things within the memory. Additionally, although certain ongoing assessment parameters may be described below in terms of receiving information via free text, multiple choice, audio, video, etc., it is recognized that any ongoing assessment parameter may be received via any suitable format.

During the ongoing assessment, the provider may set a frequency rate to retrieve the ongoing assessment parameters. The default frequency rate may be, e.g., two weeks, however, the frequency rate may be customizable (e.g., 1 week, 2 weeks, 3 weeks, 4 weeks, 6 months, or 12 months). The frequency rate may be relatively consistent or may change, e.g., based on the user's needs or how the user is progressing through treatment, for example. Based on the ongoing assessment, the provider may determine whether to adjust the frequency of the inputs from the user or request an intervention.

The process may include completing a user assessment and treatment plan (Step 218). The provider may manually input data to create and/or update the user assessment and/or treatment plan. The process may also include utilizing machine-learning models to input, add, and/or update the user assessment and/or treatment plan.

The process may include exporting a report (e.g., a history and physical report) (Step 220). The report may be based on the user assessment and/or treatment plan. The exporting may include storing and/or transmitting the report to one or more systems. The system may utilize one or more machine-learning models to generate the report. The process may include generating a document (e.g., report) in a particular format (e.g., history and physical format) that may be exported. The document may be editable by the provider. For example, the document may include a chief complaint, a history of present illness, a past psychiatric history, a past medical history, medications, substances, allergies, a past personal history, an education history, family history, psychiatric review of systems, a mental status exam, an assessment, and/or a plan of care.

Additionally, or alternatively, the process may include indicating that the consultation with the provider has completed (Step 222). In some aspects of the embodiments, the provider might be asked additional optional questions by the system that may be utilized for validating, improving, or training machine-learning models, and measuring the operational and clinical utility of the system, or specific components of it. These questions might include assessments of specific aspects of the user (for example, each functional domain) that may be used for improving the functional domain visualizations. Similarly, for any other output of the system, the provider might be asked to provide information. Such questions might relate to future outputs of the system, where the provider's input may be utilized as a ground-truth for training one or more machine-learning models.

The process may also include determining whether to admit the user to ongoing care (Step 224). Such a determination may be made by the provider. For example, the provider may analyze the user's data and the user's responses to the questions, and based on the analyzing, the provider may determine whether to complete the consultation (Step 222) or admit the user to ongoing care (Step 226). Additionally, or alternatively, the machine-learning model may analyze the user's data and the user's responses to the questions, and based on the analyzing, the machine-learning model may determine whether to complete the consultation (Step 222) or admit the user to ongoing care (Step 226).

Although FIG. 2 shows example blocks of exemplary method 200, in some implementations, the exemplary method 200 may include additional blocks, fewer blocks, different blocks, or differently arranged blocks than those depicted in FIG. 2. Additionally, or alternatively, two or more of the blocks of the exemplary method 200 may be performed in parallel.

Exemplary Method for Utilizing a Health Control System

FIG. 3A depicts a flowchart of an exemplary method 300 for utilizing a health control system, according to one or more embodiments. Method 300 may be performed by one or more processors of a server (e.g., server system 115) that is in communication with one or more user devices (e.g., user device 105), one or more provider devices (e.g., provider device 120), and other external system(s) (e.g., server system 115) via a network (e.g., network 101). However, it should be noted that process 300 may be performed by any one or more of the server, one or more user devices, or other external systems.

The method may include receiving, by one or more processors, user data from one or more first data stores (e.g., database 115A, database 110A), wherein the user data includes user health information (Step 302). The user data may include user health information, where the user health information may have been gathered as described in FIG. 2 (e.g., Steps 204, 208, 212, 218, 220). For example, the user health information may include one or more of: the user initial screening parameters, the user intake assessment parameters, the user ongoing assessment parameters, provider data, and/or user health information directly input by the user, where such information may have been previously stored in one or more data stores. In some embodiments, the user data received from the one or more first data stores may include user data from an initial user screening, as previously described.

The one or more data stores may correspond to one or more external systems (e.g., external system 110). The one or more external systems may correspond to at least one of: a health application system, a prescription system, a controlled substance tracking system, medical systems that include one or more electronic medical records, and/or local, state, and/or federal tracking systems or databases. The health application system may correspond to one or more external health applications (e.g., health mobile device applications, electronic health records) that may receive and/or store user health information (e.g., diagnoses, ailments, medications, provider notes, etc.). The prescription system may correspond to one or more external prescription systems that may receive and/or store prescription data. The prescription data may include a medication name for a current or prior prescription, a dosage amount for a current or prior prescription, prescription use information, prescription notes, prescriber information, and the like. The controlled substance tracking system may correspond to one or more external controlled substance tracking systems that receive and/or store controlled substance tracking data. For example, the controlled substance tracking data may include data regarding which users have taken controlled substances, the controlled substance description, the controlled substance amount, who prescribed the controlled substance, and/or when the user was prescribed the controlled substance. The electronic medical records may correspond to one or more healthcare systems, such as hospital systems, clinic systems, private practice systems, and/or research systems that may receive and/or store user health information (e.g., diagnoses, ailments, medications, provider notes, etc.).

In some embodiments, receiving the user data may comprise receiving, by the one or more processors, user data from at least one wearable device, wherein the at least one wearable device is configured to track user sleep data, user mobility data, and/or user electronic device consumption. The wearable device may include one or more sensors configured to track user sleep data, user mobility data, and/or user electronic device consumption. The user sleep data may include a sleep duration, a sleep onset latency, a total time in bed, a deep sleep amount, a REM sleep amount, a low heart rate during sleep, a high heart rate during sleep, an average sleep heart rate, and/or a skin temperature derivation during sleep. The user mobility data may include a high heart rate, a low heart rate, an average heart rate, an activity level, an activity duration, an oxygen level, and the like. The user electronic device consumption may include a screen time amount, an average screen time over a duration, and/or a screen time type (e.g., social media application, internet browsing, time spent working).

In some embodiments, receiving the user data (e.g., patient data) may comprise receiving by the one or more processors, the user data via the interface of the user device (e.g., user device 105). For example, the system may prompt the user (e.g., patient) for user data, such as health information that may be missing from the initial intake. Additionally, or alternatively, the system may analyze the user data received from the data stores, determine that particular user health information is missing, and then prompt the user for the missing user health information. The prompt may be output and displayed on an interface of a user device (e.g., a mobile user device). In response to the displayed prompt, the user may input user data (e.g., a response) to the prompt via the interface of the user device. The system may then receive the user data and/or store the user data in the data store.

The method may further include analyzing, by the one or more processors, the user data to determine a plurality of queries, wherein the plurality of queries include one or more audio queries, one or more text queries, and/or one or more video queries, and wherein the plurality of queries are received from a knowledge base (Step 304). The queries may correspond to user questions/prompts for additional psychiatric assessment. The knowledge base may store queries that correspond to user questions/prompts. In some embodiments, the knowledge base may be a part of a server system (e.g., server system 11). The user questions/prompts may have different forms, such as an audio form (e.g., mp3), a text form (e.g., a string of text), and/or a video form. The queries may also be directed towards various categorical information. Exemplary categories, as shown below in exemplary Table 4, may include suicidal thinking (e.g., "I often think about not being here anymore; it feels like everyone would be better off without me."), depression (e.g., "I've lost interest in activities and hobbies that I used to enjoy, nothing seems to make me happy anymore."), anxiety (e.g., "I can't stop worrying about everything, even the smallest things seem overwhelming."), ADHD (e.g., "I have a hard time focusing on tasks; my mind always seems to be jumping from one thing to another."), post-partum (e.g., "Since having my baby, I feel overwhelmingly sad and cry a lot, and it doesn't seem to get better."), acting out (e.g., "I often skip school or work without any real reason, just because I don't feel like going."), anger control (e.g., "I find myself getting unreasonably angry over minor issues and it's hard to calm down afterwards."), negative affect (e.g., "I often feel overwhelmed by intense feelings of sadness, fear, and guilt."), health problems (e.g., "I've been experiencing persistent headaches and stomach issues without any clear medical cause."), psychotic features (e.g., "I hear voices that others don't hear, and they often tell me to do things or comment on my actions."), social withdrawal (e.g., "I've been avoiding my friends and family lately; being around people just feels too overwhelming."), hostile control (e.g., "I find myself getting angry and controlling in relationships, demanding things be done my way."), alienation (e.g., "I feel like I'm completely different from everyone else, like I don't belong anywhere."), alcohol or other substance abuse problems (e.g., "I find myself drinking (or consuming/using) more often and in larger amounts than I intend to."), sleep issues (e.g., "I have trouble falling asleep almost every night, and when I do, it's a restless sleep."), and/or treatment openness (e.g., "I've been thinking that talking to a therapist or counselor might actually help me sort through my feelings and start feeling better."). Below is an expanded table of exemplary predetermined sentences for the above categories:

TABLE 4

| Indicates | Sentences |
|---|---|
| Suicidal thinking (ST) | "I often think about not being here anymore; it feels like everyone would be better off without me." |
| | "I feel so trapped and hopeless, I've started thinking about ending my life as the only way out." |
| | "I don't see any point in living; there's nothing for me in the future." |
| | "I've been making a plan to end my life, I just can't go on like this." |
| | "I've started giving my things away; I just don't need them anymore and it feels like I'm preparing for something final." |
| | "Every day, I wonder why I'm even here. What's the purpose? It feels like there's no real point to anything I do." |
| | "Lately, having a gun feels different; it's like I'm constantly reminded of a way out, an escape from all this pain." |
| Depression | "I've lost interest in activities and hobbies that I used to enjoy, nothing seems to make me happy anymore." |
| | "I feel a persistent sense of sadness and emptiness, like I'm in a deep hole I can't climb out of." |
| | "I'm constantly fatigued and have no energy, even simple tasks feel overwhelmingly difficult." |
| | "I feel worthless and hopeless about the future, as if things will never get better." |
| Anxiety | "I can't stop worrying about everything, even the smallest things seem overwhelming." |
| | "I feel restless and on edge all the time, like something bad is about to happen." |
| | "I'm having trouble sleeping because my mind won't stop racing with anxious thoughts." |
| | "I avoid social situations because I'm afraid I'll say or do something embarrassing." |
| | "I keep experiencing sudden, intense bouts of panic that make it hard to breathe and concentrate." |
| ADHD | "I have a hard time focusing on tasks; my mind always seems to be jumping from one thing to another." |
| | "Even when I try to listen carefully, I often find myself daydreaming or getting easily distracted by small things around me." |
| | "I'm constantly losing things like my keys or phone, and I struggle to organize my tasks or manage my time effectively." |
| | "I often act on impulse without thinking about the consequences, and it's hard for me to stay still for long periods." |
| Post-partum | "Since having my baby, I feel overwhelmingly sad and cry a lot, and it doesn't seem to get better." |
| | "I'm struggling to bond with my baby; I feel disconnected and like I'm not a good mother." |
| | "I'm constantly exhausted but unable to sleep, and |

TABLE 4-continued

| Indicates | Sentences |
|---|---|
| | I'm overwhelmed with anxiety about my baby's well-being." |
| | "I have intense mood swings, and sometimes I feel hopeless and think my family would be better off without me." |
| Acting out (AO) | "I often skip school or work without any real reason, just because I don't feel like going." |
| | "When I'm upset, I sometimes vandalize things or cause damage without thinking about the consequences." |
| | "I find myself getting involved in risky behaviours, like experimenting with drugs or alcohol, especially when I'm stressed." |
| | "I defy rules and instructions deliberately, especially if they come from figures of authority, like teachers or bosses." |
| Anger Control (AC) | "I find myself getting unreasonably angry over minor issues and it's hard to calm down afterwards." |
| | "When someone disagrees with me, I often respond with shouting or aggressive behaviour." |
| | "I've noticed that I hold onto grudges for a long time and struggle to let go of my anger." |
| | "I feel like my anger is out of control and it's affecting my relationships with family and friends." |
| Negative Affect (NA) | "I often feel overwhelmed by intense feelings of sadness, fear, and guilt." |
| | "I'm frequently irritable and find it hard to experience joy or pleasure in things." |
| | "I feel like I'm always on edge, and even small problems can make me feel hopeless." |
| | "I struggle with feelings of worthlessness and self-doubt on a daily basis." |
| Health Problems (HP) | "I've been experiencing persistent headaches and stomach issues without any clear medical cause." |
| | "I'm constantly tired and have trouble sleeping, which affects my day-to-day functioning." |
| | "I've noticed a significant change in my appetite, either eating too much or too little." |
| | "My chronic pain seems to be getting worse and it's impacting my ability to work or enjoy life." |
| Psychotic Features (PF) | "I hear voices that others don't hear, and they often tell me to do things or comment on my actions." |
| | "I sometimes see things that aren't there, especially when I'm alone or under stress." |
| | "I believe that people are plotting against me, even though my friends say it's not true." |
| | "I have trouble distinguishing between what's real and what's not, which is really scary." |
| Social Withdrawal (SW) | "I've been avoiding my friends and family lately; being around people just feels too overwhelming." |
| | "I no longer enjoy social gatherings; in fact, I find them exhausting and prefer to be alone." |
| | "I've lost interest in hobbies and activities I used to share with others." |
| | "I feel disconnected from everyone around me, like I just can't relate to them anymore." |
| Hostile Control (HC) | "I find myself getting angry and controlling in relationships, demanding things be done my way." |
| | "I often use intimidation or threats to get others to do what I want." |
| | "I feel the need to assert my dominance in most situations, even if it means being aggressive." |
| | "I have trouble accepting when others disagree with me and can become hostile or manipulative." |
| Alienation (AL) | "I feel like I'm completely different from everyone else, like I don't belong anywhere." |
| | "I believe that no one really understands me or cares about my experiences." |
| | "I feel isolated from the rest of the world, like I'm living in a bubble." |
| | "I distrust others and often feel that relationships are superficial and meaningless." |

TABLE 4-continued

| Indicates | Sentences |
|---|---|
| Alcohol Problems (AP) | "I find myself drinking more often and in larger amounts than I intend to." "My drinking is starting to interfere with my job and relationships, but I can't seem to stop." "I experience withdrawal symptoms like shaking and sweating if I don't drink." "I've tried to cut back on alcohol multiple times, but I always end up drinking again." |
| Sleep Issues | "I have trouble falling asleep almost every night, and when I do, it's a restless sleep." "I wake up multiple times during the night and then struggle to get back to sleep." "I feel tired all day because I can't seem to get enough restful sleep at night." "I often wake up way too early and then can't fall back asleep, no matter how tired I am." |
| Treatment openness | "I've been thinking that talking to a therapist or counselor might actually help me sort through my feelings and start feeling better." "Maybe it's time I considered getting professional help; I've heard it can make a big difference, and I'm starting to see that might be true for me." "I'm open to exploring medication if it means I can feel more like myself again; I just want to find a way to manage these overwhelming thoughts." "Seeing a psychologist or psychiatrist feels like a step in the right direction; I'm ready to understand and work through what I'm experiencing." "I've been doing some research on therapy and mental health support, and I think it's something that could be beneficial for me; I'm ready to take that step." |

The above table is exemplary only and the exact language used may differ, the order in which information is sought may differ, and other prompts/outputs or combinations of prompts/outputs may be used.

The system may analyze the user data to determine applicable user queries (e.g., questions). The questions may have a pre-set order, the order may depend on answers received to prior question(s), and/or the questions may not depend on prior answers. For example, the system may determine whether the patent health information includes particular keywords that correspond to one or more queries. In other aspects, assignment to a particular user cohort or a particular stage in an appropriate workflow may determine which queries will be output to a user. In other aspects, information or responses received from the user may be analyzed to determine one or more queries to output to a user. The queries output may therefore be predetermined or dynamic. In some embodiments, a machine-learning model may analyze the user data to determine the applicable queries or order of queries. In some embodiments, the queries may have a pre-determined order.

The machine-learning model may have been previously trained using training data to determine applicable queries. For example, the training data may have included training user health information and a training set of queries. The machine-learning model may receive the training user health information and the training set of queries, and then analyze the training user health information and the training set of queries to determine one or more relationships. The machine-learning model may then use the one or more relationships to analyze the user data to determine the applicable queries.

In some embodiments, some of the queries may include text that that is not shown to the provider. Instead, the text may be used as intermediate steps to other queries (e.g., in the tree-of-thoughts approach). The system may receive and/or generate new text (e.g., screening or intake summaries) by combining the outputs of such intermediate steps, leading to summaries that may have a consistent format. For example, the intake summary may be created so that it always starts with "Basic patient information," continues with an interpretation of an earliest memory, an analysis of functional domains, and finishes with additional insights. The system may encode the information from the intermediate steps into the knowledge base.

The method may further include outputting, by the one or more processors, the plurality of queries (e.g., user questions) via a user device, wherein the outputting includes displaying at least one of the plurality of queries on an interface of the user device and/or outputting at least one of the plurality of queries using an audio interface or a video interface of the user device (Step 306). The user questions/prompts (e.g., queries) may have different forms. For example, the user questions may have a multiple choice categorical form, where a user may be prompted to only choose one of a set of predetermined answers (e.g., the questions in the PHQ-9). The user questions may have a multiple choice hybrid form, where the user may be prompted to either choose out of predetermined answers, respond in free-text, or both. The user questions may have a free-text form, where the user may be prompted to type out the answer as free text. The user questions may have an audio form, where the question may be output using audio (e.g., the question is read by a person). The user questions may be output using different methodologies. For example, the user device may output an audio query via a speaker of the user device. The user device may output a text query by displaying the text query on the interface of the user device. The user questions may have a video form, where the user device may output the video query by displaying a video clip/video graphic on the user device. The user device may output an image-based query by displaying a still graphic on the user device.

The method may further include, in response to the outputting, receiving, by the one or more processors, user response data (e.g., user answers) from the one or more first data stores, a second data store, the interface, the audio interface, and/or the video interface of the user device (Step 308). As described above, the user response data may include a multiple choice answer, a multiple choice categorical answer, a multiple choice hybrid answer, and/or a free text answer. The user response data may include one or more of the following forms: video data, audio data, and/or text data. For example, the video data may include a video of the user responding to the question. The audio data may include an audio recording of the user responding to the question. The text data may include text the user input into the user device or selecting text on the screen of the user device. In some aspects, the user may be prompted to respond by submitting a still image such as a photograph or selfie.

In response to the outputting, the user may input user response data into the user device. For example, the user may record video data via the video interface, manually input text data (e.g., type data into the user device) via the interface, select text on the screen of the user device, record audio data via the audio interface, take photographs via a camera interface, upload pre-recorded video data from a data store of the user device, upload pre-recorded audio data from a data store of the user device, upload previously taken photographic data from a data store of the user device, and the like. Upon receiving the user response data, the system may store the user response data in one or more data stores.

In some embodiments, after receiving the user response data, the method may proceed back to Step 304. The method may include determining additional queries based on the user response data. For example, a machine-learning model may analyze the user response data and at least one of the queries to determine additional queries to output via the user device. This may occur for example, in an embodiment in which queries (e.g., personalized focused queries) are dynamically determined at least in part in response to user input received in response to one or more prior queries. For example, in a case in which incongruities were detected in a user's answers (e.g. a low PHQ-9 score-indicating healthiness, but depression related sentences were uttered by the user), then the system may recommend questions to the provider to explore depressive sentiment further. For example, if the depression related sentences were detected in the context of the patient talking about their family life, then they could be recommended a question that delves deeper into the patient's family life. Similarly, in a case in which there may be no incongruities, but the patient clearly indicates a problematic area (e.g. family life), the system may again recommend questions to the provider that delve deeper into this area of the user's life. Such questions may be referred to as personalized focused questions.

In some embodiments, receiving the user response data may include analyzing and/or processing the user response data. For example, the user response data may be analyzed and/or processed to prepare the user response data for training and utilizing the machine-learning models.

The user response data may include a categorical answer, where the categorical answer may be one-hot encoded and/or aggregated into a single score (where applicable). Aggregating the answer into a single score may be applied for sets of categorical questions that may include known psychiatric assessments (e.g., PHQ-9, ASRS, GAD-7, Edinburgh test).

The user response data may include a multiple choice hybrid answer, which may include a multiple choice answer and/or a free text answer. The hybrid answer may be represented as a combination of one-hot encoding the answers that were selected, in addition to the 64-dimensional vector representation for each free text field that was answered in free text. In some embodiments, analyzing the hybrid answer may result in one or more missing values that correspond to answers that the user did not answer in free text. The missing values may be handled differently during the application of different machine-learning processes. For example, depending on the machine learning algorithm and the results of experimentation, missing values might be filled in by a process of imputation (e.g. replacing the missing value with the average of all submissions), or the data sample might be ignored entirely during training. In some other cases, the missing value could indicate that the user refused to answer a particular question, which may be important information in and of itself, and in which case the data sample may be flagged appropriately, and the information may be utilized in subsequent steps The user response data may include a free text answer, which may be analyzed using an array of neural networks and natural language processing, in addition to extracting basic textual features, such as the following in exemplary Table 5:

TABLE 5

| NLP task | Representation |
|---|---|
| text_emotions | A vector of 7 probabilities, representing the emotions: Joy, Sadness, Anger, Disgust, Surprise, Fear, Neutral |
| text_sentiment | A vector of 3 probabilities, representing the sentiment of the transcript or the free text (negative, neutral, positive) |
| text_topic | A vector of 18 probabilities, each representing a specific topic |
| medical_entities | Two integers, representing how many treatments and how many medical problems were detected in the text |
| sentence_similarities | A vector of 16 numbers that are the result of a cosine similarity computation with a set of predetermined sentences. |
| emotional_words | A vector of 10 integers, representing the number of words that are in the text, that according to a lexicon are associated with specific emotions. |
| basic_features | A vector of 8 numbers representing: Number of characters, number of words, number of sentences, average word length, average sentence length, noun, verb, adjective distribution. |

The above table is exemplary only and the exact language used may differ, the order in which information is sought may differ, and other prompts/outputs or combinations of prompts/outputs may be used.

For example, by concatenating the vectors, each free text answer may be represented as a 64-dimensional vector. The dimensionality of the vector may change if more tasks are added, and depending on the machine-learning models used, for solving each task. Additionally, for example, in the vector representation of free text answers, the value for each category of sentence similarities may be set to the maximum cosine similarity between any sentence in the free text answer and every sentence for the query categories (e.g., suicidal thinking (e.g., "I often think about not being here anymore; it feels like everyone would be better off without me."), depression (e.g., "I've lost interest in activities and hobbies that I used to enjoy, nothing seems to make me happy anymore."), anxiety (e.g., "I can't stop worrying about everything, even the smallest things seem overwhelming."), ADHD (e.g., "I have a hard time focusing on tasks; my mind always seems to be jumping from one thing to another."), post-partum (e.g., "Since having my baby, I feel overwhelmingly sad and cry a lot, and it doesn't seem to get better."), acting out (e.g., "I often skip school or work without any real reason, just because I don't feel like going."), anger control (e.g., "I find myself getting unreasonably angry over minor issues and it's hard to calm down afterwards."), negative affect (e.g., "I often feel overwhelmed by intense feelings of sadness, fear, and guilt."), health problems (e.g., "I've been experiencing persistent headaches and stomach issues without any clear medical cause."), psychotic features (e.g., "I hear voices that others don't hear, and they often tell me to do things or comment on my actions."), social withdrawal (e.g., "I've been avoiding my friends and family lately; being around people just feels too overwhelming."), hostile control (e.g., "I find myself getting angry and controlling in relationships, demanding things be done my way."), alienation (e.g., "I feel like I'm completely different from everyone else, like I don't belong anywhere."), alcohol or substance abuse problems (e.g., "I find myself drinking or relying on substances more often and in larger amounts than I intend to."), sleep issues (e.g., "I have trouble falling asleep almost every night, and when I do, it's a restless sleep."), and/or treatment openness (e.g., "I've been thinking that talking to a therapist or counselor might actually help me sort through my feelings and start feeling better.")).

The user response data may include an audio answer and/or a video answer, which may be analyzed in a similar procedure as the free text answer. However, the audio answer and/or the video answer may also be processed using speech processing machine-learning models and information extraction procedures. For example, the audio answer and/or the video answer may be analyzed by creating an automatic transcript of the audio answer or the video answer, and then concatenating the information in the transcript into a single vector. The speech-related tasks and extracted information may include, for example, as shown in exemplary Table 6:

TABLE 6

| Key | Value |
|---|---|
| audio_emotion_class | A vector of 7 probabilities, each representing an emotion (joy, sadness, anger, fear, surprise, disgust, neutral) |
| audio_emotion_diarization | Two vectors of 7 probabilities each (representing the 7 emotions), that are the two most distant vectors that resulted from the application of the emotion divarication model |
| Audio signal features | A vector of 6 numbers representing: Duration in seconds, average loudness, average pitch, speech rate, silence ratio, average voice onset time |

The above table is exemplary only and the exact language used may differ, the order in which information is sought may differ, and other prompts/outputs or combinations of prompts/outputs may be used.

In addition to the above, each audio answer and/or video answer may end up being represented as a 91-dimensional vector.

The vector representation for each user answer may be utilized for training and inferring with various machine-learning models. An entire assessment may be represented as a feature vector by concatenating one or more of the responses in the user response data.

In some embodiments, one or more vectors representing different users' submissions may be utilized for unsupervised machine-learning processes. For example, at least one of the following unsupervised learning processes may be applied: clustering, anomaly detection, dimensionality reduction, association rule learning, and/or density estimation. Clustering algorithms may produce clusters that are meaningful to a provider, which may include the use of k-means clustering, agglomerative clustering, hierarchical clustering, and/or dbscan. The anomaly detection processes may include a vector representation that may facilitate the detection of anomalies or outliers in the data. The anomalies/outliers may be useful for showing useful information to a provider (e.g., a warning of anomalous submission) and for automatically detecting corrupted data (e.g., z-score, IQR, isolation forest, local outlier factor, and/or 1 class SVM). The dimensionality reduction process may be applied to the vector representation for the purpose of visualizing user submissions, and showing such submissions to a provider in a way in which the provider may observe meaningful information (e.g., clusters, anomalies). This may include principal component analysis and/or t-SNE. The association rule learning process may include a set of methods for detecting correlations, patterns, and/or rules within the features themselves. The rules may be useful for the internal validation and understanding of the collected data, but the rules may also be useful for a provider. For example, association rules may be computed with a variety of algorithms, such as Apriori and ECLAT. The density estimation process may include approximating or estimating the distribution of the collected data, which can subsequently be utilized for other tasks (e.g., clustering, anomaly detection, and inference). A way to estimate the density may be by using kernel density estimation.

In some embodiments, one or more supervised learning processes, which may utilize the vector representation, may be applied to the provider notes (and any annotation of data). For example, the provider's notes may be manually or automatically converted into categorical information and a vector representation of such categorical information. The vector representation may then be used for training machine-learning models for classification. For example, the process may include converting a "My Notes" section into three classes (e.g., distressed, healthy, cannot tell), and then training one or more machine-learning models to predict an annotation from the rest of the features. Such a process may include a classification algorithm, such as Naïve Bayes, decision trees, random forests, XGBoost, logistic regression, K nearest neighbors, support vector machines, and/or neural networks. Additionally, or alternatively, the "My Notes" field may be manually or automatically converted into continuous numbers, where a vector representation of the continuous numbers may be used for training regression models, such as polynomial regression, random forest regression, and/or neural networks.

In addition to being applied at the level of the entire assessment, such processes that utilize the vector representation may be also applied at the level of specific user answers for inferring potentially useful information. For example, each chief complaint may be represented as a 91-dimensional vector. As a result, it may be beneficial to apply unsupervised methods, such as clustering anomaly detection, and/or dimensionality reduction for visualization on a set of chief complaints (e.g., a set of provider user's chief complaints, a set of the system user's chief complaints, or a different subset) to provide potentially meaningful information to a provider.

Additionally, or alternatively, supervised learning methods may be applied to the data for research and validation purposes (e.g., to predict a user's PHQ-9 score from the user's chief complaint).

The method may further include creating, by the one or more processors, user overview data by applying one or more language learning models to the user response data and the user data (Step 310). The method may include retrieving the user response data from the data store, and inputting the user response data into a language learning model. Upon receiving the user response data, the language learning model may analyze the input user response data to determine user overview data. The user overview data may include a summary of the user data, where the language learning model may have been previously trained to identify relevant and pertinent information. The language learning model may then output the user overview data on a display of a provider device and/or store the user overview data in a data store.

In some embodiments, one or more language learning models may create a plurality of different user overview data. For example, the one or more language learning models may each analyze the user response data and the user data to create multiple summaries of the data. The summaries may then be input into an additional machine-learning model that may select the best summary.

The large language model (LLM) may have been trained to specifically look for incongruencies, determine and provide treatment recommendations, create and provide focused questions, and/or create and provide documentation corresponding to the user's data (e.g., answers to queries). For example, all of the user information may be represented as natural language that may not include personally identifiable information. Additional context may be inserted, where the additional context may instruct the LLM regarding how to interpret and analyze a specific piece of information. For example, when analyzing a user's earliest memory, a prompt may be added that describes how the earliest memory may be clinically analyzed. The following exemplary mapping of initial screening information ("The user is a . . . ") into natural language is shown below in exemplary Table 7:

TABLE 7

| Parameter | Value range | Text-mapping |
|---|---|---|
| Age | <N> | ". . .<N> year old. . ." |
| Sex | Male/Female/Other | ". . .Male/Female/that declared "Other" as their sex. . ." |
| Current Therapist | Y/N | ". . .that is currently/not currently seeing a therapist." |
| Current Medication | NER/Keyword <D> | "The user is on <D>." |
| Medical Issues | | "When asked to describe any medical issues. . ." |
| Medical Issues | NER (<N>) | ". . .the user mentioned <N>. . ." |
| Medical Issues | Sentence Similarity <S> | ". . .and said something similar to <S>." |
| Medical Issues | Sentiment <X> | "When describing the medical issues, the general sentiment was detected as being <X>. . ." |
| Medical Issues | Text Emotion <Z> | ". . .and the emotion was overwhelmingly/mostly <Z>." |
| Chief complaint | | "When asked why they need assistance the user submitted a recording of themselves where. . ." |
| Chief complaint | Topic <T> | ". . .the prevalent topic(s) of their submission was/were <T>." |
| Chief complaint | Audio Emotion <Y> | In this case, the emotion of the speech was detected as being overwhelmingly/mostly <Y>. . . |
| Chief complaint | Text Emotion <Z> | ". . .and the emotion in the contents of the speech was overwhelmingly/mostly <Z>. . ." |
| Chief complaint | Text Sentiment <X> | ". . .while the general sentiment was <X>." |
| Chief complaint | Sentence Similarity <S> | "The user also mentioned something along the lines of <S>." |
| ASRS | score | One the ASRS the user scored <score> that indicates. . . |
| PHQ-9 | score | On the PHQ-9 the user scored <score> that indicates. . . |
| GAD-7 | score | On the GAD-7 the user scored <score> that indicates. . . |

The above table is exemplary only and the exact language used may differ, the order in which information is sought may differ, and other prompts/outputs or combinations of prompts/outputs may be used.

The intake consultation mapping may be similar to the initial screening, however, the following intake consultation mapping, shown in exemplary Table 8, may also utilize multiple different prompts for different data samples (e.g., the earliest memory might be analyzed alone, and then in the context of the rest of the data):

TABLE 8

| Parameter | Value range | Text-mapping |
|---|---|---|
| Complaints | — | "When asked what they've been experiencing and why they are seeking help, the user submitted an audio file in which. . . |
| Complaints | Topic <T> | . . .they talked about <T>, |
| Complaints | Sentiment <S> | . . .with a general <S> sentiment. |
| Complaints | Audio Emotion <A> | The emotion(s) in their voice, were detected as being (mostly/overwhelmingly) <A>. . . |
| Complaints | Text Emotion <T> | , while in the transcript the emotions were detected as (mostly/overwhelmingly) <T> |
| Complaints | Sentence Similarity <S> | Using a sentence semantic similarity method, it was found that the user uttered sentences that were (somewhat/mostly/overwhelmingly) similar to <S>, that is an indicator of. . . (. . .) |
| Earliest memory | Instruction | The user was also asked to describe their earliest memory. Earliest autobiographical memories mark a potential beginning of our life story. . . |
| Earliest memory | Transcription <T> | When asked to describe their earliest memory, the user said <T>. . . |
| Earliest memory | Audio Emotion <A> | . . .while the emotion in their voice was detected as being (mostly/overwhelmingly) <A> |
| Primary Psychiatric Symptoms | | When asked about their psychiatric symptoms. . . |
| Primary Psychiatric Symptoms | (a) Depression patterns <D> (no free text) | . . .the user responded with <D> regarding depression patterns |
| Primary Psychiatric Symptoms | (a) Depression patterns <Df> (free text, non PII case) | . . .the user didn't choose any of the choices regarding depression patterns, instead writing down their own description, which read <Df> |
| Primary Psychiatric Symptoms | (a) Depression patterns sentence similarity <S> | . . .in which (if significantly similar sentence) the user said something similar to <S> |
| Primary Psychiatric Symptoms | (a) Depression patterns topic <T> (free text) | . . .in which (if significant topic) the user talked about <T>. . . |
| Primary Psychiatric Symptoms | (a) Depression patterns emotion <E> (free text) | . . .with a <E> emotion. . . |
| Primary Psychiatric Symptoms | (a) Depression patterns sentiment <S> (free text) | . . .and <S> general sentiment. . . |
| Primary Psychiatric Symptoms | (b) Sleep issues (if none) | The user reported no sleep issues. |
| Primary Psychiatric Symptoms | (b) Sleep issues (if i, ii, iii) | Regarding sleep issues, the user selected <answer> |
| Primary Psychiatric Symptoms | (b) Sleep issues (if iv) | Regarding sleep issues, the user reported <answer> |
| Primary Psychiatric Symptoms | (c), (d) , (e), (g), (o), (p), (q) | The user also reported having <answer> issues |
| Primary Psychiatric Symptoms | (f), (i), (j), (k), (m), (n), (s) | The user reported having <symptom>, saying specifically <answer> |
| Primary Psychiatric Symptoms | If (h) | The user reported appetite issues, specifically <answer> |
| Primary Psychiatric Symptoms | If (I) ii or iii | The user is preoccupied with weight or food, reporting <answer> |

TABLE 8-continued

| Parameter | Value range | Text-mapping |
|---|---|---|
| Primary Psychiatric Symptoms | If (I) iii | The user reported food binging, saying specifically <answer> |
| Primary Psychiatric Symptoms | (r) | The user reported having <answer> (thoughts) |
| Primary Psychiatric Symptoms | (t) alcohol | |
| Primary Psychiatric Symptoms | 3.2 | When asked when their symptoms started, the user said <answer> |
| Psychotic Symptoms | If answered | The user also reported having psychotic symptoms, specifically <answer> |
| Dissociative Symptoms | If yes | The user reported feeling like they are out of body/not present/winding up missing large parts of their time |
| Treatment History | 6 (if all no) | This is the user's first time seeking treatment. |
| Treatment History | 6.1 Therapist | |
| Treatment History | 6.2 Psychiatrist (if yes) | The user has seen a psychiatrist prior, saying <answer> |
| Treatment History | 6.3 Medication (b) | The user has taken medication prior/is currently on medication, specifically <medication table> |
| Treatment History | 6.4 Genetic Testing | |
| Treatment History | 6.5 Hospitalizations | (similar to psychiatrist, we might want to use sentence similarity instead of the user's free text answer) |
| Treatment History | 6.6 Other | |
| Medical History | 7.1 Allergies | |
| Medical History | 7.2-7.5 Issues | Regarding other medical issues, the user reported <chosen answers> |
| Medical History | 7.6 Pregnancy (if yes) | [at initial user description, from initial intake] The user is a <n> year old pregnant woman. . . |
| Medical History | 7.7 | |
| Medical History | 7.8 (other) | [Regarding other medical issues/The user also reported] <NER result/free text answer> |
| Substance History | 8.1 (caffeine) | Regarding caffeine consumption the user said <answer> |
| Substance History | If not all no | , while they reported having history with other substances, specifically |
| Substance History | 8.2 ,8.3, 8.4, 8.9, 8.10 | <substance>, for which they said <free text answer> |
| Substance History | 8.5, 8.6, 8.7, 8.8 (if yes) | <substance> |
| Substance History | 8.11, 8.12 (if yes) | Also, regarding other addictions, the user said <free text answer> |
| Personal History | 9.1 | When asked about their personal history, and their family, the user submitted an audio file in which. . . |
| Personal History | 9.1 <Audio Emotion>, <Text Emotion>, <Text Sentiment> | . . .the emotion in their voice was detected as being <audio emotion>, while in the transcription the emotion was <text emotion> while the general sentiment was detected as being <Text sentiment> |
| Personal History | 9.1 <Topic> (if not Family) | Besides their family, the user also talked about <Topic> |
| Personal History | 9.1 <sentence similarity> | , while they also said something similar to <similar sentence>, that might indicate <sentence indicates> |

TABLE 8-continued

| Parameter | Value range | Text-mapping |
|---|---|---|
| Personal History | 9.2 Parental marital status | The user's parents are <answer> |
| Personal History | 9.4, 9.9 (relationship and work status) | [at initial user description, from initial intake] The user is a. . . <relationship status> <age> <sex> <employed/unemployed> |
| Personal History | 9.3, 9.5, 9.6 (cohabitants, relationship history, children) | - [if no children]. . . with no children [otherwise]. When asked if they have children, the patient replied <children> When asked about their current living status, the patient replied <cohabitants> When asked about their relationship history, the patient said <relationship history> |
| Personal History | 9.7, 9.8, 9.12 (relationship stresses, sexual issues, work stress issues) | The user reported having <issue>, specifically saying <answer> |
| Personal History | 9.13 (if non PII we can include transcription in the prompt, otherwise ... ) | When asked what are the most important things in their life, the user submitted an audio file in which. . . |
| Personal History | 9.13 Text topic, sentence similarity | . . .the main topic of the user's response was detected as being <topic>. The user also mentioned something that was similar to <similar sentence>, that might indicate <sentence indicates> |
| Personal History | 9.13 Audio emotion, text emotion, text sentiment | In their submission, the emotion in the audio was detected as being <audio emotion>, while in the text it was <text emotion>, while the general sentiment was detected as being <text sentiment> |
| Personal History | 9.14 best qualities | When asked what are their best qualities, the user submitted an audio file in which. . . |
| Personal History | 9.14 Text topic, sentence similarity | . . .the main topic of the user's response was detected as being <topic>. The user also mentioned something that was similar to <similar sentence>, that might indicate <sentence indicates> |
| Personal History | 9.14 audio emotion, text emotion, text sentiment | In their submission, the emotion in the audio was detected as being <audio emotion>, while in the text it was <text emotion>, while the general sentiment was detected as being <text sentiment> |
| Personal History | 9.15 (significant life events) | [for each selected life event] When asked about significant life events, the patient mentioned <life event> [if further elaboration], for which they said <life event details> |
| Education History | 10.1, 10.2 | [at initial user description, from initial intake] The user is [. . .] with a high school/college/graduate level education. |
| Education History | 10.3, 10.4 | When asked about what kind of student they were at school, and what teachers said about them, the user said <answers> |
| Family History | 11.1, 11.2, 11.3, 11.4, 11.5, 11.6 (if yes) | Regarding their family's history of psychiatric issues, the user mentioned a family member having <issue> |
| PHQ-9 | score | On the PHQ-9 the user scored <score> that indicates. . . |

TABLE 8-continued

| Parameter | Value range | Text-mapping |
|---|---|---|
| GAD-7 | score | On the GAD-7, the user scored <score>, that indicates. . . |
| Functional Domains | | |
| Sentence Completion Tasks | answer | The user was also asked to complete some sentences with the first thing that came to their mind. Given the sentence <sentence>, the user replied with <answer> |

The above table is exemplary only and the exact language used may differ, the order in which information is sought may differ, and other prompts/outputs or combinations of prompts/outputs may be used.

The ongoing assessment natural language representation may start with a summary that was generated from the Intake Consultation, and then may continue with a similar mapping of the provided information into natural language, such as, for example, as shown in exemplary Table 9:

TABLE 9

| Parameter | Value range | Text-mapping |
|---|---|---|
| Check-ins | — | "When asked how they have been doing |
| Check-ins | Topic <T> | . . .the main topic(s) in their response was <T>, |
| Check-ins | Sentence Similarity <S> | . . .while they also mentioned something similar to <S>, that might indicate <Sy>. |
| Check-ins | Audio Emotion <E> | The emotion in their voice was detected as being <E>, |
| Check-ins | Text Emotion <E> | while in the content of the transcript the emotion was <E>, |
| Check-ins | Sentiment <S> | , and the general sentiment was detected as <S> |
| Check-ins | M-NER <M> | In their response, they also mentioned the following medical problems, and treatments <M> |
| Progress reporting | <answer> | When asked how would they describe their emotional status since the previous report, they chose <answer>. |
| PHQ-9, GAD-7 | <score> | The user was also asked to complete the PHQ-9/GAD-7 assessment, where they scored <score>, that indicates healthy/mild/severe depression/anxiety. In comparison, their previous PHQ-9/GAD-7 that was administered <t> weeks/months ago, had a score of <previous score> |
| Sleep data | Sleep duration <D> | Based on wearable data, the user has been sleeping on average <D> hours per night, with a maximum of <max> and a minimum of <min> in a <t> day period. |
| Sleep data | Sleep onset latency <L> | On average the sleep onset latency was <L> minutes |
| Sleep data | Sleep.deep, sleep.REM | , while <deep> hours of deep sleep, and <rem> hours of REM sleep were registered. |

TABLE 9-continued

| Parameter | Value range | Text-mapping |
|---|---|---|
| Sleep data | Hr_lowest, hr_average | Their lowest heartrate registered during sleep was <lowest>, while on average their heartrate was <average> |
| Functional Domain Assessment | <answer> | Concerning their functional domains, the user selected <answer(s)> |
| Sentence completion | <answer> | Finally, the user was asked to complete the sentence(s) <sentences>, to which they replied with <answer>. |

The above table is exemplary only and the exact language used may differ, the order in which information is sought may differ, and other prompts/outputs or combinations of prompts/outputs may be used.

After representing the available information into natural language, such a representation may be used as part of a prompt with specific task instructions for the machine-learning model. For example, the prompt may include one or more of the following: an input-output prompt, a persona instruction, a response formatting, a few shot, a chain-of-thought prompt, a self-consistency prompt, a tree of thought prompt, and/or an iterative refinement prompt.

In some embodiments, the method may include generating and/or outputting one or more functional domain visualizations. The system may include four types of inputs that are related to the function domains: (1) direct inputs (e.g., answers to direct questions per the functional domains), (2) indirect inputs (e.g., answers to indirect questions per the functional domain), (3) narrative inputs (e.g., anything detected in the narrative relating to one of the function domains), and/or (4) contextual inputs (e.g., answers to questions that relate to the context of a domain, such as work-related stresses, relationship history, important family members, and the like). The functional domain data may be represented as one or more values (e.g., corresponding a direct signal and/or an indirect signal), where one or more machine-learning models may analyze user data and make one or more inferences to determine the functional domain data values. For example, the one or more machine-learning models may receive some or all of the user responses to the queries and/or additional contextual user data to determine the functional domain data values, where the functional domain data values may be converted (e.g., based on a scale) to a corresponding label. Exemplary labels may include one or more of the following labels: (1) "likely not a problem area;" (2) "likely a problem area;" and/or (3) "risk of under reporting of potential problems."

The functional domain visualizations may be displayed to the provider in one or more formats, where the visualizations may be based on the values described above. The formats may include a cartesian coordinate system, where the horizontal axis may represent the direct signal, going from "negative" or "problematic" to the left and "positive" or "healthy" to the right. The value of the direct signal may correspond to the result of querying the knowledge base. Similarly, the vertical axis may represent the indirect signal, going from "negative" or "problematic" at the bottom, and "positive" or "healthy" at the top. Such visualizations may be displayed via one or more user interfaces of a device. Given this coordinate system, and the calculation of the "indirect signal" and "direct signal", each functional domain may be mapped to a point in the coordinate system, and shown to the provider.

For example, FIG. 3B depicts an exemplary dashboard 320 that includes one or more functional domains, according to one or more embodiments. The functional domains may include a visual indicator, such as a color-coding scheme, that corresponds to the particular label. For example, in a color-coding scheme, the color red may be used for when a particular area is likely a problem area, the color green may be used for when a particular area is likely not a problem area, and/or the color yellow may be used for a risk of under reporting of potential problems. Although colors and example colors are provided, other visual indicators, such as patterns, the size of graphics, the type of graphics, etc., may be used to indicate a particular label for data. In some aspects, the labels themselves may be used in addition to the visual indicators, or the labels may be used instead of visual indicators. Additionally, or alternatively, the functional domains may include one or more direct inquiries and/or one or more indirect inquiries, where the direct queries show user responses to direct questions and the indirect queries show user responses to indirect questions. The functional domains may indicate exemplary results to the direct inquiries and/or indirect inquiries.

An exemplary prototypical example 322 is shown in FIG. 3C, according to one or more embodiments. For example, the coordinate system might be labeled as shown in FIG. 3C, explaining the different areas of the plot. The different areas might also be color coded. The plot might be shown rotated by 90 degrees, so that the "supported positive" label is at the top. The visualization might be interactive, where mousing over or clicking on the icon corresponding to a domain would initiate a pop up window showing all information that might have been utilized for inferring the coordinates for a particular domain. Besides the grid visualization, the functional domains might be visualized in more conventional ways at different places in the platform, such as a table including the direct and/or indirect results in separate columns (in addition to any other columns that might be deemed important), or a list of cards for each functional domain, where each card might include information related to that specific domain.

The method may further include determining, by the one or more processors, whether the user overview data includes one or more incongruencies by applying one or more trained first machine-learning models to the user overview data (Step 312). The trained machine-learning models may analyze the user overview data to determine one or more incongruencies in the user overview data. As discussed herein, the one or more trained first machine-learning models may have been previously trained to determine the one or more incongruencies.

In some embodiments, in response to determining that the user overview data does not include the one or more incongruencies, outputting, by the one or more processors, an incongruency alert indicating that the user overview data does not include the one or more incongruencies. For example, the incongruency alert may be displayed on a provider device, where the incongruency alert may indicate that no incongruencies were found and that the user may continue treatment.

In some embodiments, determining the one or more incongruencies may comprise applying, by the one or more processors, the one or more trained machine-learning models to the user overview data to analyze user specific data, wherein the user specific data includes user body language, a user tone, a user speech frequency, a user appearance, a user facial expression, a user response content, and/or a user location, for example. The user body language may correspond to the user's body language in video data or in a still image data (user response data) when responding to the one or more queries. The user tone may correspond to the user's tone in video data and/or audio data (user response data) when responding to the one or more queries. The user speech frequency may correspond to the user's speech frequency (e.g., speech patterns, speech pacing) in video data and/or audio data (user response data) when responding to the one or more queries. The user appearance may correspond to the user's appearance (e.g., disheveled clothes, unkempt appearance) in video data (user response data) when responding to the one or more queries. The user facial expression may correspond to the user's facial expressions (e.g., strained smile, no smile) in video or still image data (user response data) when responding to the one or more queries. The user response content may correspond to the content (e.g., word choice, word patterns) in video data, audio data, and/or text data (user response data) when responding to the one or more queries. The user location may correspond to the location of the user when the user made the video data, the audio data, and/or the text data (user response data) when responding to the one or more queries.

The trained machine-learning models may have been previously trained to determine incongruencies within the data. For example, the trained machine-learning models may determine that a user tone is inconsistent with the user response. In some embodiments, the machine-learning models may have been previously trained based on provider input and/or user data. Additionally, the trained-machine learning models may have been trained using one or more rules to detect the incongruencies, as described in the next section of this disclosure.

In some embodiments, the method may further include retrieving, by the one or more processors, one or more rules from the knowledge base. The method may further include applying, by the one or more processors, via the one or more trained machine-learning models, the one or more rules to determine the one or more incongruencies. The rules may have been previously created and stored in the knowledge base. For example, when a user gives a "Healthy" answer to a "Categorical, Direct, DepressionRelated" question, and an "AudioDistressed" answer to any "Audio" question, then the trained machine-learning model may identify an "Audio Affect Depression Incongruency." In some embodiments, the rules may correspond to whether a user was flagged as having a particular disorder.

In some embodiments, the method may include applying one or more density estimation algorithms to the user data to estimate a probability distribution of various aspects of the user's responses. For example, the knowledge base may include information about "depression related answers," "depression related questions," and/or how the user responds to each (e.g., affect, sentiment, affirmation). All of this information can be heuristically mapped to values representing the continuum from "distressed" to "healthy." Given a set of such values, applying a density estimation algorithm may provide a visualization of the assumed distribution to the provider in a plot.

FIG. 3D depicts an exemplary visualization plot 330, according to one or more embodiments. For example, FIG. 3D illustrates an estimated distribution of depression-related patient responses. A peak towards the left (marked "distressed" on the x-axis) may be interpreted as a high probability that a depression-related user response indicates distress, whereas a peak to the right (marked "healthy" on the x-axis) may indicate a high probability that a depression-related response may indicate healthiness (with respect to depression). In the particular example shown in FIG. 3D, there are two peaks, one corresponding to the "distressed" area and one corresponding to the "healthy" area which may be higher, while the area under the curve in the "healthy" range may be larger than the one in the "distressed" range. For example, if the system selects a depression-related user response at random, there may be a higher probability of the user response indicating healthiness as opposed to distress. However, the existence of a peak in the "distressed" range may indicate that there may be a significant number of depression-related patient responses that indicate distress. This may indicate that that there may be an incongruity in the user's self-report, and through interactions with the visualization, the provider may be able to delve into the user responses to see the origin of the distress, as well as decide if this may be a situation of underreporting depression. As an example, PHQ9 may usually be interpreted as a single score, where two users might have the same score with different responses. When estimating the distribution of responses, a user who responded "several days" to hall the questions and "more than half the days" to the other half might result in a figure with a peak in the middle (as these responses may not strongly indicate either depression nor healthiness). On the other hand, a user that responded "not at all" to half the questions and "nearly every day" to the other half, even though the user would have the same PHQ9 score as the first user, the estimated distribution may include two peaks, one corresponding to the "distressed" range and one corresponding to the "healthy" range (since "not at all" may indicate healthiness, and "nearly every day" may indicate distress). The existence of two peaks for the second patient may communicate to the provider that there may be a significant chance that the user may be experiencing distress, and it may also indicate incongruity and may call the reliability of the user's self-report into question. For example, the user could be underreporting or overreporting. By interacting with the visualization, the provider may quickly get a better understanding of the user's current experience. This may not be possible using more traditional approaches. In general, the shape of the distribution may illustrate congruity. A distribution shifted to the right may indicate possible healthiness, a distribution shifted to the left may indicate possible distress, while a bimodal distribution may indicate incongruity. What comprises a "depression related response" may be defined through the knowledge graph. For example, it could be a response to a depression related question, or it could be a depression-indicating response to a different question. Although depression is depicted in FIG. 3D, such graphical visualizations and synthesized data may be generated for any suitable psychological or behavioral indication, such as ADHD, eating disorders, etc.

For example, one or more waves might be generated for any aspect the user's responses for which the knowledge base includes information. For example, the system may include a visualization for each symptom, for each functional domain, for each significant clinical dimension, and the like. In some embodiments, the waves might be interactive, where if the provider mouses over different parts of the plot, the display may show information corresponding to which patient responses contributed the most to that particular part of the plot. In the context of ongoing care, the waves might be animated to highlight temporal changes in user responses.

In some embodiments, training the one or more trained machine-learning models may comprise receiving, by a machine-learning model, a user test overview and a plurality of test incongruencies. The training may further comprise training the machine-learning model to determine one or more associations between the user test overview and the plurality of test incongruencies.

The method may further include, in response to determining inclusion of the one or more incongruencies, extracting, by the one or more processors, via one or more trained second machine-learning models, the user overview data that corresponds to the one or more incongruencies (Step 314). The one or more trained second machine-learning models may have been previously trained to determine the user overview data that corresponds to the one or more incongruencies. The extracted user overview data may provide context regarding an incongruency. Using the example described above, if there is an "Audio Affect Depression Incongruency," the extracted user overview data may include data regarding the "Healthy" answer, the "Audio-Distressed" answer, and video data that indicates that the user's appears disheveled and tired.

The method may further include generating, by the one or more processors, an alert by applying the one or more trained first machine-learning models to the user overview data and the one or more incongruencies, if included (Step 316). The alert may include a summary of the user data, a summary of the incongruencies and extracted overview data, and/or an assessment recommendation regarding how to proceed with the user. For example, the recommendation may include whether the user should be given a referral to another provider, should stay with the current provider, needs immediate medical attention, and the like. The alert may assist a provider by providing the data regarding the detected incongruencies. In some embodiments, the machine-learning model may generate an alert with incongruencies that are more urgent than others.

In some embodiments, the method may include updating, in real time, the summary data. The updating may be in response to the system receiving data from the user and/or the provider. The machine-learning models may summarize and deprioritize older information when compared to newer information.

In some embodiments, the alert, queries, or anything else, may be tailored to each provider. For example, such data may be tailored to a provider based on the provider's years of experience, areas of expertise, and the like. For example, "patients" may be referred to as "clients" for therapists. Additionally, or alternatively, a feature may be added where, via a slider, a provider may modify the tone of the language within a summary. The method may include utilizing one or more machine-learning models to modify the tone of the language within a summary. Another example may relate to treatment recommendations, where the system may recommend a CBT approach for a therapist that prefers Cognitive Behavioral Therapy (CBT). In contrast, the system may recommend a more relational or dynamic approach for a therapist that prefers such an approach.

In some embodiments, the alert may include a prioritization of users. For example, the machine-learning models may analyze the user overview data, the one or more incongruencies, user overview data of one or more additional users, and one or more incongruencies of the one or more additional users. Based on the analysis, the machine-learning model may then prioritize the users (e.g., from most urgent to least urgent), where the alert may include the prioritization of the users.

The method may further include outputting, by the one or more processors, the alert to a display of a provider device (Step 318). For example, a summary of the incongruencies and a description of the assessment recommendation may be displayed on a provider's mobile device or computer.

In some embodiments, the method may include, in response to outputting the alert, receiving, by the one or more processors, expert feedback indicating an accuracy of the alert from the provider device. For example, in addition to displaying the alert, the system may also display a feedback indicator (e.g., thumbs up, thumbs down) on the provider device. The provider may select the feedback indicator to indicate an accuracy of the alert. The system may receive the feedback and store the feedback in a data store for training the machine-learning model.

The method may further include training, by the one or more processors, the one or more trained machine-learning models based on the expert feedback. The feedback may be retrieved from the data store, and then input into the machine-learning model for additional training. The machine-learning model may receive the feedback, the alert (e.g., the summary of the user data, the assessment recommendation, as well as a summary of the incongruencies and extracted overview data), the user data, and/or the plurality of queries. Based on the input information, the machine-learning model may analyze the information to improve the accuracy of the machine-learning model.

In some embodiments, the alert may include a spreadsheet of vectors that correspond to the user response data. The vectors may include a numerical representation of the user response data. The vectors may be used as input to further train the machine-learning models.

In some embodiments, the method may include analyzing, by the one or more processors, via the one or more trained machine-learning models, the user overview data to determine a customized user overview. The method may further include, in response to the analyzing, creating, by the one or more processors, via the one or more trained machine-learning models, an electronic communication (e.g., an email) based on the customized user overview. The method may further include outputting, by the one or more processors, via the one or more machine-learning models, the electronic communication to the provider device.

In some embodiments, the method may further include storing, by the one or more processors, the user response data, the user overview data, and the one or more incongruencies in the one or more data stores. The stored data may be used to track a user's progress. For example, the system may refer back to the stored incongruencies to see if the user's behavior changes over time.

In some embodiments, the method may further include generating, by the one or more processors, a visual representation that corresponds to the extracted user overview data that corresponds to the one or more incongruencies. The method may further include outputting, by the one or more processors, the visual representation on the provider device. The visual representation may include a chart, a graph, a graphic, a video, and the like.

In some embodiments, the method may include generating summary data (e.g., a report) that includes information approved by the clinician and/or spoken/messaged by the clinician and/or shared with the user. The summary data may correspond to the user's therapeutic progress, a reflection on the user's past responses, and/or any other information that the provider may deem important to share with the user. Additionally, or alternatively, one or more machine-learning models and/or other system components may suggest and/or generate the summary data based on stored data and/or the interactions between the clinician and the user. The summary data may include video data. For example, the provider may communicate asynchronously (e.g., ongoing assessments, what the provider is learning about the user) via video of the provider speaking. The system (e.g., one or more machine-learning models) may create and/or recommend a script to the provider, where they system may facilitate recording and/or editing of the video data.

Although FIG. 3A shows example blocks of exemplary method 300, in some implementations, the exemplary method 300 may include additional blocks, fewer blocks, different blocks, or differently arranged blocks than those depicted in FIG. 3A. Additionally, or alternatively, two or more of the blocks of the exemplary method 300 may be performed in parallel.

Exemplary Knowledge Base

The knowledge base may have been constructed by symbolically encoding relevant knowledge. For example, the information that flows through the knowledge base may be separated into the following categories: categorical self-reported, narrative self-reported, implied self-reported, objective information, directly inferred information, and/or provider inferred information. The categorical self-reported category may include structured information that a user has chosen out of predetermined answers (e.g., PHQ-9, ASRS, and the like). The narrative self-reported category may include information that the user has chosen to divulge in a free text field, an audio field, and/or a video field. Symbolic information may be extracted through sentence similarities and/or topic classification. The implied self-reported category may include information that the user has implied in a free text field, an audio field, and/or a video field, without explicitly stating the information. Symbolic information may be extracted through sentiment and/or emotion classification. The objective information category may include information that is objective, such as sleep data. The directly inferred information category may include information that was inferred directly using predetermined rules, predetermined incongruencies, and the like. The indirectly inferred information category may include information that was inferred indirectly, according to the judgment of an LLM or another "black-box" model (SCTs and earliest memory analysis, summary analysis). The provider inferred information may include information that was inferred by a human medical expert. The categorical self-reported category, the narrative self-reported category, the implied self-reported category, and the objective information category may include structured gathered data (e.g., multiple-choice, sleep issues), in addition to the structure information that may have been extracted from raw inputs. The directed inferred information category and the indirectly inferred information category may include inferred information that was either directly inferred or indirectly inferred, including the heuristics for enabling a provider to detect phenomena of illusory mental health, for all three levels of abstraction (machine-learning, knowledge representation, LLM).

In some embodiments, the machine-learning model may have been previously trained to modify information within the queries and/or information received from the user to conform to data standards (e.g., HIPPA). For example, the representation of a query into text may follow the generic format: "The patient was asked <question>, for which <context>, and the patient replied <answer>". The "context" part of the representation may be encoded into the knowledge base, where the knowledge base may include information regarding why a particular question was asked, in addition to information regarding how an answer to this question should be interpreted. The <context> might not be needed for some questions, while it may be extensive for other questions, such as the entire contents of a research paper. Any context for any of these questions may have been encoded into the knowledge base.

The information in the knowledge base may be encoded into a knowledge graph. For example, the knowledge base information may be encoded using terminology that may be defined in the knowledge base, such as concepts, roles, and/or individuals, as described below.

The knowledge base may describe a hierarchy of concepts related to different types of questions. For example, the following concepts may be used to characterize a question: (1) pertaining to a possible type of answer (mutually disjoint) (e.g., CategoricalQuestion, FreeTextQuestion, HybridQuestion, AudioQuestion); (2) pertaining to whether the question is direct or indirect (mutually disjoint) (e.g., DirectQuestion, IndirectQuestion); and/or (3) pertaining to whether the question is related to a specific disorder (not mutually disjoint) (e.g., DepressionRelatedQuestion, Anxiety RelatedQuestion, ADHDRelatedQuestion). In the context of the knowledge base, there may be one individual answer for each question that might have been defined in each of the assessments. Additionally, or alternatively, there might be concepts that are subsumed by, or that subsume, the concepts described in this disclosure (e.g., "DisorderRelatedQuestion" or "ADHDHyperActiveRelatedQuestion").

The knowledge base may describe a set of concepts related to different types of answers. The following concepts may be used to describe different types of answers: (1) pertaining to indication of distress (mutually disjoint) (e.g., HealthyAnswer, MildDistressAnswer, ModerateDistressAnswer, SevereDistressAnswer); (2) pertaining to the detection of emotions (not mutually disjoint) (e.g., JoyfulAudioAnswer, JoyfulTextAnswer); and/or (3) pertaining to the semantic similarity of the answer with predetermined sentences (not mutually disjoint) (e.g., DepressionIndicatingAnswer, ADHDIndicatingAnswer).

The knowledge base may also include a defined set of roles that may be used for defining semantic relationships between individuals. For example, the "hasGivenAnswer" role may connect users to their answers, the "isAnswerTo" may connect answers to questions, and the "isPartOfAssessment" may connect questions to assessments.

The individuals in the knowledge base may correspond to individual user names and/or user identifier (e.g., patient identifier). For example, a user's name or identifier may be associated with each of the user's answers, with each assessment, and/or with each question.

In some embodiments, the knowledge base may encode additional information. For example, the additional information may include the following information: (1) pertaining to the topics detected in the answer (not mutually disjoint) (e.g., RealtionshipsTopicAnswer, DailyLifeTopicAnswer); and/or (2) pertaining to medical entities detected in the answer (not mutually disjoint) (e.g., TreatmentContainingAnswer (AntidepressantMentioningAnswer), ProblemContainingAnswer (DepressionMentioningAnswer)).

The knowledge base may include one or more layers that may correspond to the organization, structuring, and/or analysis of available user information. Such layers may include a present illness and timeline layer (layer 1), a daily life layer (functional domains) (layer 2), and/or a core personality, associations, and/or subconscious layer (layer 3). The present illness and timeline layer may include information related to the user's "surface level" present illness, symptoms, and the corresponding timeline. For example, queries that correspond to this layer may relate to primary psychiatric symptoms, dissociative symptoms, treatment history, medical history, and/or substance history of the user. The daily life layer may correspond to information related to the user's daily life, family, work, relationships, leisure, enjoyment, hope, mood, finances, and the like. For example, queries that correspond to this layer may relate to personal history, education history, family history, functional domain assessment, sentence completion test, and the like. For example, a user presenting with anxiety (layer 1) that has a strong social support circle (layer 2), but experiences work related stress (layer 2), may be different than a user presenting with anxiety (layer 1), has a satisfying career (layer 2), but struggles with relationships (layer 2), and the therapeutic avenues may be different for these two users, despite them being "identical" on the surface (layer 1). The core personality, associations, and/or subconscious layer may correspond to the user's core personality traits, which might be uncovered through projective tests and associations. For example, queries that correspond to this layer may correspond to the user's earliest memory and/or new questions.

A provider might choose to filter through the information in each layer. For example, there may be a "present illness timeline" dashboard (layer 1), which may include a summary, visualizations, recommended questions, potential areas of concern, treatment recommendations, and the like, relating to the present illness. There may be a dashboard tab for functional domains, with its own summary, visualization and/or abstraction of information, and a final summary for the core personality. These dashboard tabs may persist and evolve during the ongoing care, and they may be separate of the main "preview/overview" tab of the dashboard that may display a high level of information.

For example, FIG. 3E depicts an exemplary user dashboard 340, according to one or more embodiments. The user dashboard 340 may include the user's information (e.g., user name), the user's raw responses to the queries, one or more assessments and/or plans, and/or a consultation report. The user dashboard 340 may also include one or more user specific summaries. The one or more trained machine-learning models may analyze the user's responses to the queries, and then based on the analysis, generate summary data that includes the most relevant and/or important data for the particular section of the dashboard 340. For example, the machine-learning models may analyze the user responses and/or corresponding patient data to determine a personal life history and/or treatment recommendations. The machine-learning models may provide an unbiased summary, where the machine-learning models may have been previously trained to identify pertinent information that may be useful in providing a summary of user specific data. Additionally, or alternatively, the user dashboard 340 may include the previously described functional domains, the below-described potential areas of concern, and/or user self-reported scores (e.g., scores for PHQ-9, GAD-7, and/or ASRS).

The summaries may provide an efficient and accurate way for the gathering and synthesis of the user's raw data. The provider may be able to validate the provider's assessments against the summaries (e.g., ground truth). For example, the use of machine-learning models may provide for more efficient insights, as the machine-learning models are able to provide the summaries in a shorter period of time.

In some embodiments, the methods described herein may include detecting one or more flags (e.g., using a rule-based approach and/or a machine-learning model) during a user screening, and displaying such flags to the provider via a provider dashboard. The one or more flags may correspond to one or more of the following categories: (1) self-report skew, (2) impulsivity, (3) personality pathology, (4) substance use, and/or (5) eating disorders. Such flags may correspond to specific questions answered in the screening, as shown in the following exemplary Table 10:

TABLE 10

| Question | Categories | Flag |
|---|---|---|
| Have you ever shaded the truth to get out of a difficult situation? | Direct report skew | Skew-healthy self-reporting |
| I have never had a happy day in my life | Direct report skew | Skew-unhealthy self-reporting |
| My drug use gets me into trouble | Substance use | Problematic drug use |
| I drink too much | Substance use | Problematic drinking |
| No matter what I do or who I am with, I feel empty | Personality pathology | Feels empty |
| People always leave me, and I don't know why | Personality pathology | Feels abandoned |
| Sometimes I harm myself to relieve tension. | Impulsivity, Personality pathology | Risk of self-harm |
| My friends think I drink too much or use too many drugs | Substance use | Friends concerned about substance use |
| I get enraged when people disappoint me | Personality pathology | Anger management |
| People have told me that I do dangerous things | Impulsivity | Dangerous or risky behaviors |
| My attitude towards food is worrisome | Impulsivity, Eating disorder | Problematic relationship with food |
| No matter what people say, I don't like the way my body looks | Impulsivity, Eating disorder | Body image |

Additionally, or alternatively, the methods may also include detecting a flag corresponding to "directly inferred information" in the user data. The system may display the flags to a provider via a dashboard on a display of a user device.

FIG. 3F depicts an exemplary user interface 350 that indicates potential areas of concern, according to one or more embodiments. For example, the system may output one or more flags (e.g., corresponding to the one or more "Flags" in Table 10) and one or more labels (e.g., corresponding to the "Categories" in Table 10) to a user interface of the device.

FIG. 4 illustrates an exemplary graph 400 that outlines exemplary user response relationships, according to one or more embodiments. Additionally, given a number of different questions and question types, such a graph may become quite complex and utilized for graph machine learning. For example, in response to one or more displayed questions, a user may provide one or more answers to the system (402). For example, the user may provide an answer to an ASRS question (404), where the answer is a healthy answer (406). The system may determine that the ASRS answer is an answer to an ASRS question (408), where the ASRS question is an ADHD related question (410), a categorical question (412), and a direct question (414).

The user may also provide an answer to an ADHD cohort question (416), where the answer is an ADHD indicating answer (418) to a joyful audio question (420). The ADHD cohort answer may be an answer to a specific ADHD cohort indirect question (e.g., question 1.1) (422), which may be an ADHD related question (424), an audio question (426), and an indirect question (428).

In some embodiments, one or more of the following processes may be utilized for inferring and extracting information from the graph: node classification, link prediction, graph embedding, graph clustering, and/or anomaly detection. The node classification process may involve automatically classifying nodes into specific classes, where such processes may utilize a populated, annotated graph for supervised training. For example, the nodes may represent users, answers, and/or questions, where node classification may include classifying users, questions, or answers into categories. For example, training a node classification model may include utilizing annotations submitted by providers via a "My Notes" field and/or via other methods (e.g., thumbs up, thumbs down, a user's engagement with the platform, etc.). The link prediction process may involve automatically predicting the existence of edges (e.g., roles) between nodes. Such processes may include learning representations of the knowledge base links connecting users to answers, answers to questions, and questions to assessments. The graph embedding process may involve transforming nodes, edges, and their features into a low-dimensional space while preserving the graph's structural information. This may facilitate tasks like similarity searching, clustering, and link prediction by enabling the application of machine-learning algorithms on graph data. The graph clustering process may detect clusters of nodes that may have similar labels and connections. The anomaly detection process may utilize the graph structure.

The knowledge base may include an ABox, where the ABox may include assertions about the world that are being described in the knowledge base. For example, this may include expressions of the form C (a) or r (a, b), where C may correspond to a concept name, r may correspond to a role name, and a, b may correspond to individual names. In the ABox, each available piece of information may be asserted, such as assertions about each question and the question type. Additionally, as users answer questions, the information about each answer, including the result of the extracted information, may be encoded as an assertion with the ABox, including the role assertions that connect user to answers and answers to questions.

In some embodiments, before making the assertions, some information may be pre-processed in order for the information to be represented symbolically. For example, various questionnaires that may have pre-defined scoring guidelines (e.g., PHQ-9, GAD-7) may be pre-processed, where the scores may be converted into concepts relating to levels of distress. Additionally, for example, sleep data (e.g., "REM sleep time" and "sleep time onset") from a wearable device may be converted into higher-level concepts, such as "SleepIssues."

Additionally, or alternatively, the knowledge base may include a TBox, where the TBox may include terminological axioms that may define additional concepts of the knowledge base. The terminological axioms may be utilized by a reasoner, where additional inferred concepts may be output to the provider. The following axioms may be defined:

Categorical-Narrative Incongruencies—A categorical-narrative incongruency may be determined when a user's response to a categorical question indicates healthiness regarding a particular disorder, but the user may have also indicated distress for the disorder in a narrative answer. In particular, as an example for depression: DepressionCategoricalNarrativeIncongruencyPatient$\sqsubseteq\exists$BhasGivenAnswer. (HealthyAnswer∩∃isAnswerTo. (CategoricalQuestion∩DepressionRelatedQuestion))∩∃hasGivenAnswer. (DepressionIndicatingAnswer). Similar axioms may be defined for the following categories that may have categorical questions related to a disorder and/or ways of detecting disorder indications within a user's narrative response: ADHD, anxiety, post-partum, psychotic features, sleep issues, and/or primary psychiatric symptoms.

Categorical-Implied Incongruencies—A categorical-implied incongruency may be determined when a user's response to a categorical question indicates distress, but the user's affect (implied in a different narrative question) indicates healthiness, or vice versa. Such incongruencies may relate to the user's apparent affect contrasted against the user's categorical self-report. In particular: DepressionNegativeAffectIncongruencyPatient⊆∃hasGivenAnswer. (HealthyAnswer∩∃isAnswerTo.(CategoricalQuestion∩DepressionRelatedQuestion))∩∃hasGivenAnswer. (NegativeAffectAnswer). Similarly, when the categorical response indicates distress, but the apparent affect indicates healthiness: DepressionPositiveAffectIncongruencyPatient⊆∃hasGivenAnswer.(DistressedAnswer∩∃isAnswerTo. (CategoricalQuestion∩DepressionRelatedQuestion))∩∃ hasGivenAnswer.(PositiveAffectAnswer).

Categorical-Objective Incongruencies—The categorical-objective incongruencies are similar to the categorical-implied incongruencies, but the categorical-objective incongruencies involve objective information (e.g., sleep data).

Self-Consistency Incongruencies—A self-consistency incongruency may be determined when the same piece of information is acquired from different answers. For example, the voice emotions of a user's response may be compared with the text emotions and sentiment to determine if the response is the same. For example, the following pertains to voice versus text content affect at a specific answer: AudioTextAffectIncongruencyPatient⊆∃hasGivenAnswer.(PositiveAudioAffectAnswer∩Negative TextAffectAnswer), AudioTextAffectIncongruencyPatient⊆∃hasGivenAnswer.(NegativeAudioAffectAnswer∩Positive TextAffectAnswer). The following pertains to the voice affect at a specific answer: IntraAudioAffectIncongruencyPatient⊆∃hasGivenAnswer.(PositiveAudioAffect Answer∩NegativeAudioAffectAnswer). The following pertains to the text affect at a specific answer: IntraTextAffectIncongruencyPatient⊆∃hasGivenAnswer.(PositiveTextAffectAnswer∩Negative TextAffectAnswer). The following pertains to a voice affect at different answers: InterAudioAffectIncongruencyPatient⊆∃hasGivenAnswer. (PositiveAudioAffectAnswer∩∃hasGivenAnswer.(NegativeAudioAffectAnswer). The following pertains to the text affect at different answers: InterTextAffectIncongruencyPatient⊆∃hasGivenAnswer.(PositiveTextAffectAnswer⊆∃ hasGivenAnswer.(Negative TextAffectAnswer).

Pertaining to voice vs text content affect at a specific answer: AudioTextAffectIncongruencyPatient⊆∃hasGivenAnswer.(PositiveAudioAffectAnswer∩NegativeTextAffectAnswer). AudioTextAffectIncongruencyPatient⊆∃hasGivenAnswer. (NegativeAudioAffectAnswer∩PositiveTextAffectAnswer). Pertaining to voice affect at a specific answer: IntraAudioAffectIncongruencyPatient⊆∃hasGivenAnswer.(PositiveAudioAffectAnswer∩NegativeAudioAffectAnswer). Pertaining to text affect at a specific answer: IntraTextAffectIncongruencyPatient⊆∃hasGivenAnswer. (PositiveTextAffectAnswer∩NegativeTextAffectAnswer). Pertaining to voice affect at different answers: InterAudioAffectIncongruencyPatient⊆∃hasGivenAnswer.(PositiveAudioAffectAnswer)∩∃hasGivenAnswer.(NegativeAudioAffectAnswer). Pertaining to text affect at different answers: InterTextAffectIncongruencyPatient⊆∃hasGivenAnswer. (PositiveTextAffectAnswer∩∃hasGivenAnswer.(Negative TextAffectAnswer)

Exemplary Device

Figure 5:
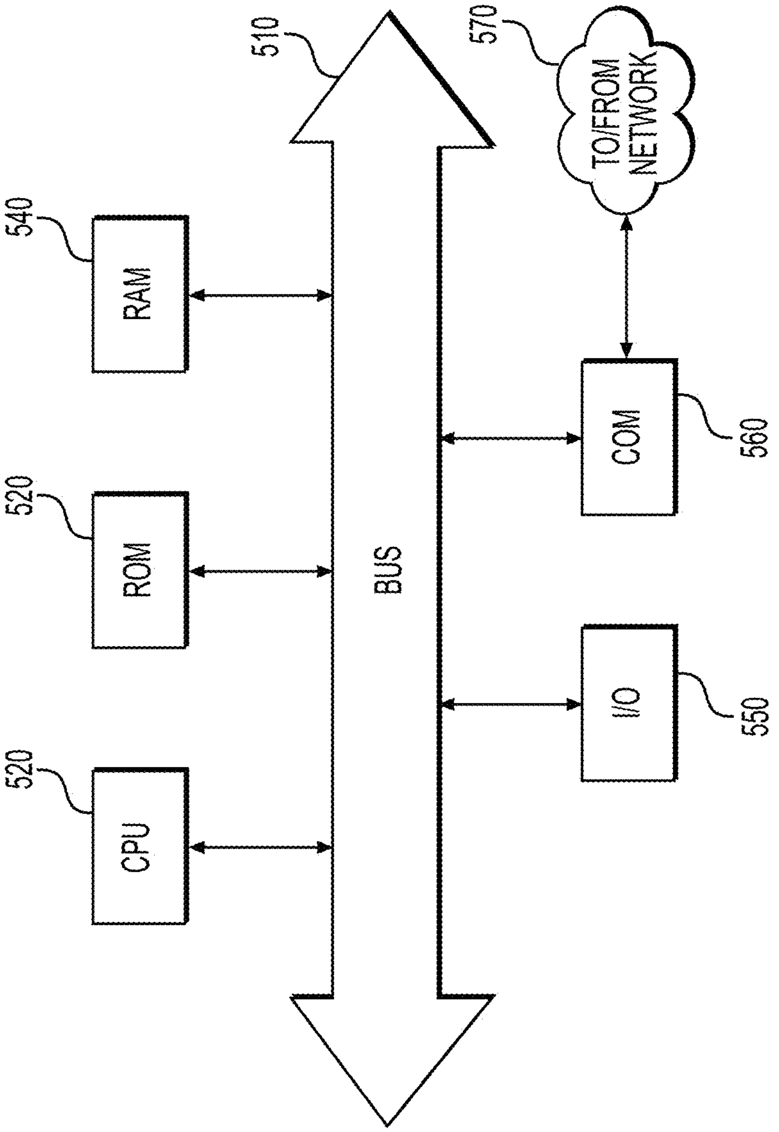
FIG. 5 depicts an example of a computing device that may execute the techniques described herein, according to one or more embodiments.

FIG. 5 is a simplified functional block diagram of a computer 500 that may be configured as a device for executing the methods of FIGS. 2-4, according to exemplary embodiments of the present disclosure. For example, device 500 may include a central processing unit (CPU) 520. CPU 520 may be any type of processor device including, for example, any type of special purpose or a general-purpose microprocessor device. As will be appreciated by persons skilled in the relevant art, CPU 520 also may be a single processor in a multi-core/multiprocessor system, such system operating alone, or in a cluster of computing devices operating in a cluster or server farm. CPU 520 may be connected to a data communication infrastructure 510, for example, a bus, message queue, network, or multi-core message-passing scheme.

Device 500 also may include a main memory 540, for example, random access memory (RAM), and also may include a secondary memory 530. The device 500 may receive programming and data via network communications 570. Secondary memory 530, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage unit may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 530 may include other similar means for allowing computer programs or other instructions to be loaded into device 500. Examples of such means may include a program cartridge and cartridge interface (such as that found in video game devices), a removable memory chip (such as an EPROM, or PROM) and associated socket, and other removable storage units and interfaces, which allow software and data to be transferred from a removable storage unit to device 500.

Device 500 also may include a communications interface ("COM") 560. Communications interface 560 allows software and data to be transferred between device 500 and external devices. Communications interface 560 may include a modem, a network interface (such as an Ethernet card), a communications port, a PCMCIA slot and card, or the like. Software and data transferred via communications interface 560 may be in the form of signals, which may be electronic, electromagnetic, optical, or other signals capable of being received by communications interface 560. These signals may be provided to communications interface 560 via a communications path of device 500, which may be implemented using, for example, wire or cable, fiber optics, a phone line, a cellular phone link, an RF link or other communications channels.

The hardware elements, operating systems and programming languages of such equipment are conventional in nature, and it is presumed that those skilled in the art are adequately familiar therewith. Device 500 also may include input and output ports 550 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

Reference to any particular activity is provided in this disclosure only for convenience and not intended to limit the disclosure. A person of ordinary skill in the art would recognize that the concepts underlying the disclosed devices and methods may be utilized in any suitable activity. The disclosure may be understood with reference to the following description and the appended drawings, wherein like elements are referred to with the same reference numerals.

The terminology used above may be interpreted in its broadest reasonable manner, even though it is being used in conjunction with a detailed description of certain specific examples of the present disclosure. Indeed, certain terms may even be emphasized above; however, any terminology intended to be interpreted in any restricted manner will be overtly and specifically defined as such in this Detailed Description section. Both the general description and the detailed description are exemplary and explanatory only and are not restrictive of the features, as claimed.

It should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Thus, while certain embodiments have been described, those skilled in the art will recognize that other and further modifications may be made thereto without departing from the spirit of the invention, and it is intended to claim all such changes and modifications as falling within the scope of the invention. For example, functionality may be added or deleted from the block diagrams and operations may be interchanged among functional blocks. Steps may be added or deleted to methods described within the scope of the present invention.

The above disclosed subject matter is to be considered illustrative, and not restrictive, and the appended claims are intended to cover all such modifications, enhancements, and other implementations, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations are possible within the scope of the disclosure. Accordingly, the disclosure is not to be restricted except in light of the attached claims and their equivalents.

What is claimed is:

1. A computer-implemented method for utilizing a health control system, the computer-implemented method comprising:

receiving, by one or more processors, user data from one or more first data stores, wherein the user data includes user health information;

analyzing, by the one or more processors, the user data to determine a plurality of queries, wherein the plurality of queries include one or more audio queries, one or more text queries, and/or one or more video queries, and wherein the plurality of queries are received from a knowledge base;

outputting, by the one or more processors, the plurality of queries via a user device of a user, wherein the outputting includes displaying at least one of the plurality of queries on an interface of the user device and/or outputting at least one of the plurality of queries using an audio interface or a video interface of the user device;

in response to the outputting, receiving, by the one or more processors, user response data of the user from the one or more first data stores, a second data store, the interface, the audio interface, and/or the video interface of the user device, wherein the user response data includes a plurality of user responses, and wherein the plurality of user responses includes audio response data, textual response data, or video response data;

converting, by the one or more processors, the audio response data, the textual response data, or the video response data for the plurality of user responses into a corresponding audio response vector, a textual response vector, or a video response vector;

concatenating, by the one or more processors, the audio response vector, the textual response vector, or the video response vector for the plurality of user responses to create a vector representation for each of the plurality of user responses;

applying, by the one or more processors, an anomaly detection process to the vector representation for each of the plurality of user responses to detect an outlier for any of the plurality of user responses, wherein the applying the anomaly detection process includes:

creating one or more nodes corresponding to the user data, at least one of the plurality of user responses, or at least one of the plurality of queries, classifying, utilizing a node classification model, the one or more nodes based on a user category, a query category, or a response category, the node classification model previously trained to perform the classification based on a populated graph including one or more annotations, predicting one or more edges between the one or more classified nodes based on one or more knowledge base links, transforming the one or more nodes and the one or more edges into a low-dimensional space, and determining the outlier by applying the transformed one or more nodes and transformed one or more edges to the vector representation;

creating, by the one or more processors, user overview data by applying one or more language learning models to the user response data, the vector representation for each of the plurality of user responses, and the user data;

determining, by the one or more processors, whether the user overview data includes one or more incongruencies by applying one or more trained first machine-learning models to the user overview data, wherein the one or more incongruencies include a categorical-narrative incongruency, a categorical-implied incongruency, a categorical-objective incongruency, and/or a self-consistency incongruency;

in response to determining inclusion of the one or more incongruencies, extracting, by the one or more processors, via one or more trained second machine-learning models, the user overview data that corresponds to the one or more incongruencies;

inputting, by the one or more processors, the user overview data, the one or more incongruencies, additional user overview data of one or more additional users, and one or more additional user incongruencies corresponding to the one or more additional users into one or more trained third machine-learning models configured to output an urgency priority of the user and the one or more additional users;

receiving, by the one or more processors, the urgency priority from the one or more trained third machine-learning models;

generating, by the one or more processors, summary data by applying the one or more trained first machine-learning models to the user overview data and the one or more incongruencies; and outputting, by the one or more processors, an alert to a display of a provider device, wherein the alert includes the summary data, the urgency priority, and the outlier for at least one of the plurality of user responses.

2. The computer-implemented method of claim 1, wherein determining whether the user overview data includes the one or more incongruencies of the user overview data comprises:

applying, by the one or more processors, the one or more trained first machine-learning models to the user overview data to analyze user specific data, wherein the user specific data includes one or more of user body language, a user tone, a user speech frequency, a user appearance, a user facial expression, user response content, and/or a user location.

3. The computer-implemented method of claim 2, further comprising:

retrieving, by the one or more processors, one or more rules from the knowledge base; and applying, by the one or more processors, via the one or more trained first machine-learning models, the one or more rules to determine the one or more incongruencies.

4. The computer-implemented method of claim 1, wherein receiving the user data further comprises:

receiving, by the one or more processors, additional user data from at least one wearable device, wherein the at least one wearable device is configured to track user sleep data, user mobility data, and/or user electronic device consumption.

5. The computer-implemented method of claim 1, wherein receiving the user data comprises:

receiving by the one or more processors, the user data via the interface of the user device.

6. The computer-implemented method of claim 1, wherein the one or more first data stores correspond to one or more external systems, wherein the one or more external systems correspond to at least one of: a health application system, a prescription system, a controlled substance tracking system, and/or a medical system.

7. The computer-implemented method of claim 1, wherein training the one or more trained first machine-learning models comprises:

receiving, by a machine-learning model, a user test overview and a plurality of test incongruencies; and training the machine-learning model to determine one or more associations between the user test overview and the plurality of test incongruencies.

8. The computer-implemented method of claim 1, further comprising:

in response to outputting the alert, receiving, by the one or more processors, expert feedback indicating an accuracy of the alert from the provider device; and training, by the one or more processors, the one or more trained first machine-learning models based on the expert feedback.

9. The computer-implemented method of claim 1, wherein outputting the alert to the display of the provider device further comprises:

analyzing, by the one or more processors, via the one or more trained first machine-learning models, the user overview data to determine a customized user overview;

in response to the analyzing, creating, by the one or more processors, via the one or more trained first machine-learning models, an electronic communication based on the customized user overview; and outputting, by the one or more processors, via the one or more trained first machine-learning models, the electronic communication to the provider device.

10. The computer-implemented method of claim 1, further comprising:

storing, by the one or more processors, the user response data, the user overview data, and the one or more incongruencies in the one or more first data stores.

11. The computer-implemented method of claim 1, wherein outputting the alert on the display of the provider device further comprises:

generating, by the one or more processors, a visual representation that corresponds to the extracted user overview data that corresponds to the one or more incongruencies; and outputting, by the one or more processors, the visual representation on the provider device.

12. The computer-implemented method of claim 1, wherein the user data received from the one or more first data stores is user data from an initial user screening.

13. The computer-implemented method of claim 1, wherein the one or more trained first machine-learning models have been previously trained to determine the one or more incongruencies.

14. The computer-implemented method of claim 1, wherein the one or more trained second machine-learning models have been previously trained to determine the user overview data that corresponds to the one or more incongruencies.

15. The computer-implemented method of claim 1, further comprising:

in response to determining that the user overview data does not include the one or more incongruencies, outputting, by the one or more processors, an incongruency alert indicating that the user overview data does not include the one or more incongruencies.

16. A computer system for utilizing a health control system, the computer system comprising:

a memory having processor-readable instructions stored therein; and one or more processors configured to access the memory and execute the processor-readable instructions, which, when executed by the one or more processors, configures the one or more processors to perform a plurality of functions, including functions for:

receiving user data from one or more first data stores, wherein the user data includes user health information;

analyzing the user data to determine a plurality of queries, wherein the plurality of queries include one or more audio queries, one or more text queries, and/or one or more video queries, and wherein the plurality of queries are received from a knowledge base;

outputting the plurality of queries via a user device of a user, wherein the outputting includes displaying at least one of the plurality of queries on an interface of the user device and/or outputting at least one of the plurality of queries using an audio interface or a video interface of the user device;

in response to the outputting, receiving user response data of the user from the one or more first data stores, a second data store, the interface, the audio interface, and/or the video interface of the user device wherein the user response data includes a plurality of user responses, and wherein the plurality of user responses includes audio response data, textual response data, or video response data;

converting the audio response data, the textual response data, or the video response data for the plurality of user responses into a corresponding audio response vector, a textual response vector, or a video response vector;

concatenating the audio response vector, the textual response vector, or the video response vector for the plurality of user responses to create a vector representation for each of the plurality of user responses;

applying an anomaly detection process to the vector representation for each of the plurality of user responses to detect an outlier for any of the plurality of user responses, wherein the applying the anomaly detection process includes:

creating one or more nodes corresponding to the user data, at least one of the plurality of user responses, or at least one of the plurality of queries, classifying, utilizing a node classification model, the one or more nodes based on a user category, a query category, or a response category, the node classification model previously trained to perform the classification based on a populated graph including one or more annotations, predicting one or more edges between the one or more classified nodes based on one or more knowledge base links, transforming the one or more nodes and the one or more edges into a low-dimensional space, and determining the outlier by applying the transformed one or more nodes and transformed one or more edges to the vector representation;

creating user overview data by applying one or more language learning models to the user response data, the vector representation for each of the plurality of user responses, and the user data;

determining whether the user overview data includes one or more incongruencies by applying one or more trained first machine-learning models to the user overview data, wherein the one or more incongruencies include a categorical-narrative incongruency, a categorical-implied incongruency, a categorical-objective incongruency, and/or a self-consistency incongruency;

in response to determining inclusion of the one or more incongruencies, extracting, via one or more trained second machine-learning models, the user overview data that corresponds to the one or more incongruencies;

inputting the user overview data, the one or more incongruencies, additional user overview data of one or more additional users, and one or more additional user incongruencies corresponding to the one or more additional users into one or more trained third machine-learning models configured to output an urgency priority of the user and the one or more additional users;

receiving the urgency priority from the one or more trained third machine-learning models;

generating summary data by applying the one or more trained first machine-learning models to the user overview data and the one or more incongruencies; and outputting an alert to a display of a provider device, wherein the alert includes the summary data, the urgency priority, and the outlier for at least one of the plurality of user responses.

17. The computer system of claim 16, wherein determining inclusion of the one or more incongruencies of the user overview data comprises:

applying the one or more trained first machine-learning models to the user overview data to analyze user specific data, wherein the user specific data includes one or more of user body language, a user tone, a user speech frequency, a user appearance, a user facial expression, a user response, user response content, and/or a user location.

18. The computer system of claim 17, the functions further comprising:

retrieving one or more rules from the knowledge base; and applying, via the one or more trained first machine-learning models, the one or more rules to determine inclusion of the one or more incongruencies.

19. The computer system of claim 16, wherein receiving the user data further comprises:

receiving additional user data from at least one wearable device, wherein the at least one wearable device is configured to track user sleep data, user mobility data, and/or user electronic device consumption.

20. The computer system of claim 16, wherein receiving the user data comprises:

receiving the user data via the interface of the user device.

21. A non-transitory computer-readable medium containing instructions for utilizing a health control system, the instructions comprising:

receiving, by one or more processors, user data from one or more first data stores, wherein the user data includes user health information;

analyzing, by the one or more processors, the user data to determine a plurality of queries, wherein the plurality of queries include one or more audio queries, one or more text queries, and/or one or more video queries, and wherein the plurality of queries are received from a knowledge base;

outputting, by the one or more processors, the plurality of queries via a user device of a user, wherein the outputting includes displaying at least one of the plurality of queries on an interface of the user device and/or outputting at least one of the plurality of queries using an audio interface or a video interface of the user device;

in response to the outputting, receiving, by the one or more processors, user response data of the user from the one or more first data stores, a second data store, the interface, the audio interface, and/or the video interface of the user device, wherein the user response data includes a plurality of user responses, and wherein the plurality of user responses includes audio response data, textual response data, or video response data;

converting, by the one or more processors, the audio response data, the textual response data, or the video response data for the plurality of user responses into a corresponding audio response vector, a textual response vector, or a video response vector;

concatenating, by the one or more processors, the audio response vector, the textual response vector, or the video response vector for the plurality of user responses to create a vector representation for each of the plurality of user responses;

applying, by the one or more processors, an anomaly detection process to the vector representation for each of the plurality of user responses to detect an outlier for any of the plurality of user responses, wherein the applying the anomaly detection process includes:

creating one or more nodes corresponding to the user data, at least one of the plurality of user responses, or at least one of the plurality of queries, classifying, utilizing a node classification model, the one or more nodes based on a user category, a query category, or a response category, the node classification model previously trained to perform the classification based on a populated graph including one or more annotations, predicting one or more edges between the one or more classified nodes based on one or more knowledge base links, transforming the one or more nodes and the one or more edges into a low-dimensional space, and determining the outlier by applying the transformed one or more nodes and transformed one or more edges to the vector representation;

creating, by the one or more processors, user overview data by applying one or more language learning models to the user response data, the vector representation for each of the plurality of user responses, and the user data;

determining, by the one or more processors, whether the user overview data includes one or more incongruencies by applying one or more trained first machine-learning models to the user overview data, wherein the one or more incongruencies include a categorical-narrative incongruency, a categorical-implied incongruency, a categorical-objective incongruency, and/or a self-consistency incongruency;

in response to determining inclusion of the one or more incongruencies, extracting, by the one or more processors, via one or more trained second machine-learning models, the user overview data that corresponds to the one or more incongruencies;

inputting, by the one or more processors, the user overview data, the one or more incongruencies, additional user overview data of one or more additional users, and one or more additional user incongruencies corresponding to the one or more additional users into one or more trained third machine-learning models configured to output an urgency priority of the user and the one or more additional users;

receiving, by the one or more processors, the urgency priority from the one or more trained third machine-learning models;

generating, by the one or more processors, summary data by applying the one or more trained first machine-learning models to the user overview data and the one or more incongruencies; and outputting, by the one or more processors, an alert to a display of a provider device, wherein the alert includes the summary data, the urgency priority, and the outlier for at least one of the plurality of user responses.

22. The non-transitory computer-readable medium of claim 21, the instructions further comprising:

in response to outputting the alert, receiving, by the one or more processors, expert feedback indicating an accuracy of the alert from the provider device; and training, by the one or more processors, the one or more trained first machine-learning models based on the expert feedback.

23. The non-transitory computer-readable medium of claim 21, the instructions further comprising:

storing, by the one or more processors, the user response data, the user overview data, and the one or more incongruencies in the one or more data stores.

* * * * *